United States Patent
Engstrand et al.

(10) Patent No.: US 10,076,416 B2
(45) Date of Patent: *Sep. 18, 2018

(54) MOSAIC IMPLANTS, KITS AND METHODS FOR CORRECTING BONE DEFECTS

(71) Applicant: OSSDSIGN AB, Uppsala (SE)

(72) Inventors: Thomas Engstrand, Uppsala (SE); Jan Bohlin, Harbo (SE); Jonas Åberg, Uppsala (SE); Håkan Engqvist, Uppsala (SE)

(73) Assignee: OSSDSIGN AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/767,253

(22) PCT Filed: Feb. 12, 2014

(86) PCT No.: PCT/IB2014/000780
§ 371 (c)(1),
(2) Date: Aug. 11, 2015

(87) PCT Pub. No.: WO2014/125381
PCT Pub. Date: Aug. 21, 2014

(65) Prior Publication Data
US 2015/0374497 A1    Dec. 31, 2015

Related U.S. Application Data

(60) Provisional application No. 61/826,489, filed on May 22, 2013, provisional application No. 61/802,228, (Continued)

(51) Int. Cl.
*A61F 2/02* (2006.01)
*A61F 2/28* (2006.01)
(Continued)

(52) U.S. Cl.
CPC .......... *A61F 2/2846* (2013.01); *A61B 17/688* (2013.01); *A61B 17/8085* (2013.01);
(Continued)

(58) Field of Classification Search
CPC ................. A61F 2/2875; A61F 2/2846; A61F 2002/30561; A61F 2002/30466;
(Continued)

(56) References Cited

U.S. PATENT DOCUMENTS

| 4,839,215 A | 6/1989 | Starling et al. |
| 4,905,679 A | 3/1990 | Morgan |

(Continued)

FOREIGN PATENT DOCUMENTS

| CN | 2607960 Y | 3/2004 |
| CN | 1919357 A | 2/2007 |

(Continued)

OTHER PUBLICATIONS

Bohner et al, J. Biomaterials, 26(33):6423-6429 (2005).
(Continued)

*Primary Examiner* — Brian Dukert
(74) *Attorney, Agent, or Firm* — Porter Wright Morris & Arthur LLP

(57) ABSTRACT

A mosaic implant conformable to a curved surface, comprising first and second implant sections coupled along a beam portion extending across a length of the implant, each of the implant sections having—a plurality of biocompatible mosaic plates, and—a plurality of wires which interconnect the plates with one another. The mosaic implant is configured to be deformable such that at least a portion of the mosaic implant is conformable to a curved surface, with the beam portion providing structural support which resists inward deformation of the curved portion of the implant. A
(Continued)

kit for forming a mosaic implant is also provided, along with a method for correcting a bone defect in a patient.

22 Claims, 25 Drawing Sheets

Related U.S. Application Data filed on Mar. 15, 2013, provisional application No. 61/763,942, filed on Feb. 12, 2013.

(51) Int. Cl.
    *A61B 17/68*     (2006.01)
    *A61B 17/80*     (2006.01)
    *A61F 2/30*     (2006.01)

(52) U.S. Cl.
CPC .............. *A61F 2/28* (2013.01); *A61F 2/2875* (2013.01); *A61F 2/30965* (2013.01); *A61F 2002/3092* (2013.01); *A61F 2002/3096* (2013.01); *A61F 2002/30143* (2013.01); *A61F 2002/30324* (2013.01); *A61F 2002/30451* (2013.01); *A61F 2002/30462* (2013.01); *A61F 2002/30578* (2013.01); *A61F 2002/30957* (2013.01); *A61F 2002/30985* (2013.01); *A61F 2310/00353* (2013.01)

(58) Field of Classification Search
CPC .... A61F 2002/30907; A61F 2002/2878; A61F 2002/2882; A61F 2002/2885; A61F 2002/2889; A61B 17/688; A61B 17/8085; Y10S 606/903
See application file for complete search history.

(56) References Cited

U.S. PATENT DOCUMENTS

| | | |
|---|---|---|
| 5,139,497 A | 8/1992 | Tilghman et al. |
| 5,152,836 A | 10/1992 | Hirano et al. |
| 5,201,737 A | 4/1993 | Leibinger et al. |
| 5,338,356 A | 8/1994 | Hirano et al. |
| 5,368,602 A | 11/1994 | De la Torre |
| 5,372,598 A | 12/1994 | Luhr et al. |
| 5,380,328 A | 1/1995 | Morgan |
| 5,468,242 A * | 11/1995 | Reisberg ............ A61B 17/8085 606/151 |
| 5,503,164 A | 4/1996 | Freidman |
| 5,545,226 A | 8/1996 | Wingo et al. |
| 5,605,713 A | 2/1997 | Boltong |
| 5,683,667 A | 11/1997 | Fulmer et al. |
| 5,690,631 A | 11/1997 | Duncan et al. |
| 5,702,419 A | 12/1997 | Berry et al. |
| 5,743,913 A | 4/1998 | Wellisz |
| 5,752,958 A | 5/1998 | Wellisz |
| 5,766,176 A | 6/1998 | Duncan |
| 5,782,971 A | 7/1998 | Constantz et al. |
| 5,783,217 A | 7/1998 | Lee et al. |
| 5,785,712 A | 7/1998 | Runciman et al. |
| 5,814,048 A | 9/1998 | Morgan |
| 5,876,447 A | 3/1999 | Arnett |
| 5,980,540 A | 11/1999 | Bruce |
| 5,984,925 A | 11/1999 | Apgar |
| 6,068,656 A | 5/2000 | Von Oepen |
| 6,071,291 A | 6/2000 | Forst et al. |
| 6,093,188 A | 7/2000 | Murray |
| 6,117,456 A | 9/2000 | Lee et al. |
| 6,206,957 B1 | 3/2001 | Wenz et al. |
| 6,299,635 B1 | 10/2001 | Frantzen |
| 6,338,810 B1 | 1/2002 | Carpena |
| 6,344,055 B1 | 2/2002 | Shukov |
| 6,364,881 B1 | 4/2002 | Apgar et al. |
| 6,521,246 B2 | 2/2003 | Sapieszko et al. |
| 6,642,285 B1 | 11/2003 | Bohner et al. |
| 6,685,707 B2 | 2/2004 | Roman et al. |
| 6,719,795 B1 | 4/2004 | Cornwall et al. |
| 6,733,582 B1 | 5/2004 | Bohner et al. |
| 6,863,899 B2 | 3/2005 | Koblish et al. |
| 6,905,516 B1 | 6/2005 | Lemaitre et al. |
| 6,991,803 B2 | 1/2006 | Sapieszko et al. |
| 7,118,705 B2 | 10/2006 | Lin |
| 7,175,858 B2 | 2/2007 | Contantz et al. |
| 7,252,841 B2 | 8/2007 | Constantz et al. |
| 7,318,841 B2 | 1/2008 | Totighi et al. |
| 7,341,601 B2 | 3/2008 | Eisermann et al. |
| 7,351,262 B2 | 4/2008 | Bindseil et al. |
| 7,351,280 B2 | 4/2008 | Khairoun et al. |
| 7,407,542 B2 | 8/2008 | Lemaitre et al. |
| 7,473,312 B2 | 1/2009 | Barralet et al. |
| 7,501,018 B2 | 3/2009 | Engqvist et al. |
| 7,625,399 B2 | 12/2009 | Case et al. |
| 7,655,047 B2 | 2/2010 | Swords |
| 7,682,400 B2 | 3/2010 | Zwirkoski |
| 7,754,246 B2 | 7/2010 | Mosley et al. |
| 7,833,253 B2 | 11/2010 | Ralph et al. |
| 7,927,363 B2 | 4/2011 | Perouse |
| 8,043,382 B2 | 10/2011 | Kumar et al. |
| 8,231,624 B1 | 7/2012 | Strippgen |
| 8,246,663 B2 | 8/2012 | Lovald et al. |
| 8,281,638 B2 | 10/2012 | Metzger |
| 8,287,915 B2 | 10/2012 | Clineff et al. |
| 8,298,292 B2 | 10/2012 | Swords et al. |
| 8,361,126 B2 | 1/2013 | Perrow et al. |
| 8,366,751 B2 | 2/2013 | Pfefferle |
| 8,398,720 B2 | 3/2013 | Swords |
| 8,403,965 B2 | 3/2013 | Henderson et al. |
| 8,435,265 B2 | 5/2013 | Konieczynski et al. |
| 8,556,990 B2 | 10/2013 | Bartee et al. |
| 8,795,377 B2 | 8/2014 | Engqvist et al. |
| 8,834,611 B1 | 9/2014 | Dimicelli |
| 8,906,074 B2 | 12/2014 | Kang et al. |
| 9,023,085 B2 | 5/2015 | Strippgen |
| 2001/0011188 A1 | 8/2001 | Berry et al. |
| 2002/0151965 A1 | 10/2002 | Roth |
| 2003/0082232 A1 | 5/2003 | Lee et al. |
| 2003/0199615 A1 | 10/2003 | Chaput et al. |
| 2003/0208262 A1 | 11/2003 | Gaber |
| 2004/0261356 A1 | 12/2004 | Wrass |
| 2005/0149032 A1 | 7/2005 | Vaughen et al. |
| 2005/0216008 A1 | 9/2005 | Zwimmann et al. |
| 2005/0261780 A1 | 11/2005 | Heino et al. |
| 2005/0288790 A1 | 12/2005 | Swords |
| 2006/0224242 A1 | 1/2006 | Longo |
| 2006/0116682 A1 | 6/2006 | Longo |
| 2006/0235542 A1 | 10/2006 | Hodorek et al. |
| 2006/0239884 A1 | 10/2006 | Chane-Ching et al. |
| 2006/0263443 A1 | 11/2006 | Chow et al. |
| 2007/0092856 A1 | 4/2007 | Chow et al. |
| 2007/0112434 A1 | 5/2007 | Hakamatsuka et al. |
| 2007/0156146 A1 | 7/2007 | Metzger et al. |
| 2007/0173844 A1 | 7/2007 | Ralph et al. |
| 2007/0189951 A1 | 8/2007 | Constantz et al. |
| 2007/0233264 A1 | 10/2007 | Nycz et al. |
| 2007/0233272 A1 | 10/2007 | Boyce et al. |
| 2008/0009872 A1 | 1/2008 | Vaughen et al. |
| 2008/0027455 A1 | 1/2008 | Bondeville |
| 2008/0028992 A1 | 2/2008 | Lee et al. |
| 2008/0053940 A1 | 3/2008 | Whalen et al. |
| 2008/0187571 A1 | 8/2008 | Clineff et al. |
| 2008/0206300 A1 | 8/2008 | Bohner et al. |
| 2009/0022771 A1 | 1/2009 | Lynn et al. |
| 2009/0076617 A1 | 3/2009 | Ralph et al. |
| 2009/0099409 A1 | 4/2009 | Luehrs et al. |
| 2009/0216338 A1 | 8/2009 | Gingras et al. |
| 2009/0220475 A1 | 9/2009 | Bohner et al. |
| 2009/0237880 A1 | 9/2009 | Levesque et al. |
| 2009/0317447 A1 | 9/2009 | Levesque et al. |
| 2010/0095870 A1 | 2/2010 | Insley et al. |
| 2010/0069455 A1 | 3/2010 | Takato et al. |
| 2010/0069913 A1 | 3/2010 | Chirico et al. |
| 2010/0094428 A1 | 4/2010 | Ralph et al. |
| 2010/0269736 A1 | 10/2010 | Chow et al. |

(56) References Cited

U.S. PATENT DOCUMENTS

| | | |
|---|---|---|
| 2010/0303888 A1 | 12/2010 | Barralet et al. |
| 2011/0014244 A1 | 1/2011 | Sapieszko et al. |
| 2011/0054540 A1 | 3/2011 | Ralph et al. |
| 2011/0152195 A1 | 6/2011 | O'Mahony et al. |
| 2011/0158963 A1 | 6/2011 | Font Perez et al. |
| 2011/0218626 A1 | 9/2011 | Krinke et al. |
| 2012/0058152 A1* | 3/2012 | Garcia de Castro Andrews ......... A61F 2/02 424/400 |
| 2012/0165957 A1 | 6/2012 | Everland et al. |
| 2012/0226320 A1 | 9/2012 | Kang et al. |
| 2012/0265312 A1 | 10/2012 | Burke et al. |
| 2012/0271418 A1 | 10/2012 | Hollister et al. |
| 2012/0289964 A1 | 11/2012 | Nakaji |
| 2012/0310365 A1 | 12/2012 | Chaput et al. |
| 2013/0053900 A1 | 2/2013 | Qwarnstrom et al. |
| 2013/0066325 A1 | 3/2013 | Engqvist et al. |
| 2013/0138114 A1 | 5/2013 | Lin et al. |
| 2013/0158670 A1 | 6/2013 | Tigno, Jr. |
| 2014/0027333 A1 | 1/2014 | Pawlowski et al. |
| 2014/0172116 A1 | 6/2014 | Maxson et al. |
| 2014/0206273 A1 | 7/2014 | Larsen et al. |
| 2014/0228969 A1 | 8/2014 | Engstrand et al. |
| 2014/0243993 A1 | 8/2014 | Barrett et al. |
| 2014/0288650 A1 | 9/2014 | Hunt |
| 2014/0316472 A1 | 10/2014 | Rise et al. |
| 2015/0105806 A1 | 4/2015 | Dorafshr et al. |

FOREIGN PATENT DOCUMENTS

| | | |
|---|---|---|
| CN | 101360461 A | 2/2009 |
| CN | 101528158 A | 9/2009 |
| DE | 29913334 U1 | 9/1999 |
| EP | 543765 A1 | 5/1993 |
| EP | 544384 B1 | 1/1996 |
| EP | 433852 B1 | 3/1996 |
| EP | 433852 B2 | 3/1996 |
| EP | 1023032 B1 | 1/2002 |
| EP | 910993 B1 | 7/2002 |
| EP | 984745 B1 | 10/2003 |
| EP | 936929 B1 | 6/2004 |
| EP | 1380313 B1 | 5/2005 |
| EP | 1178847 B1 | 1/2007 |
| EP | 1905368 A1 | 4/2008 |
| EP | 1420725 B1 | 8/2008 |
| EP | 1958580 A1 | 8/2008 |
| EP | 2014258 A1 | 1/2009 |
| EP | 2030596 A1 | 3/2009 |
| EP | 1298103 B1 | 5/2011 |
| EP | 2474286 A1 | 7/2012 |
| EP | 2529702 A1 | 12/2012 |
| JP | 1-100049 A | 4/1989 |
| JP | 2-143945 U | 12/1990 |
| JP | 2006-218050 A | 8/2006 |
| JP | 2007/501054 A | 1/2007 |
| WO | 95/20368 A1 | 8/1995 |
| WO | 02/11781 A1 | 2/2002 |
| WO | 02/22045 A1 | 3/2002 |
| WO | 03/007831 A1 | 1/2003 |
| WO | 2004/093734 A2 | 11/2004 |
| WO | 2004/108019 A2 | 12/2004 |
| WO | 2004/112859 A1 | 12/2004 |
| WO | 2005/016616 A1 | 2/2005 |
| WO | 2005/074453 A2 | 8/2005 |
| WO | 2005/077049 A2 | 8/2005 |
| WO | 2005-122956 A2 | 12/2005 |
| WO | 2007/047921 A2 | 4/2007 |
| WO | 2008/002595 A2 | 1/2008 |
| WO | 2009/077210 A1 | 6/2009 |
| WO | 2010/055483 A2 | 5/2010 |
| WO | 2010/092001 A1 | 8/2010 |
| WO | 2011/009635 A1 | 1/2011 |
| WO | 2011/068451 A2 | 6/2011 |
| WO | 2011/112145 A1 | 9/2011 |
| WO | 2011112145 A1 | 9/2011 |
| WO | WO 2011112145 A1 * | 9/2011 ......... A61B 17/8085 |
| WO | 2012/016200 A1 | 2/2012 |
| WO | 2012/103164 A1 | 8/2012 |
| WO | 2012/118843 A1 | 9/2012 |
| WO | 2012/147114 A1 | 11/2012 |
| WO | 2014091469 A1 | 6/2014 |

OTHER PUBLICATIONS

Xu et al. Journal of Materials Science; Materials in Medicine, 18(7); 1345-1353 (2007).
Barralet et al, J. Biomaterials, 25(11 );2197-2203 (2004).
Habraken et al, Advance Drug Delivery Reviews, 59(4-5);234-248 (2007).
Han et al. Acta Biomaterialia, 5;3165-3177 (2009).
Desai et al. Advances in Bioceramics and Biocomposites II, Ceramic Engineering and Science Proceedings, vol. 27, Issue 6, Wereszczak et al, Editor, Wiley, pp. 61-69 (Nov. 2006).
Hirayama et al. Journal of Research of the National Institute of Standards and Technology, 113(6);311-320 (2008).

* cited by examiner

MOSAIC IMPLANTS, KITS AND METHODS FOR CORRECTING BONE DEFECTS

CROSS REFERENCE TO RELATED APPLICATIONS

This application claims priority to U.S. Provisional Patent Application Nos. 61/763,942, filed on Feb. 12, 2013, entitled "MOSAIC IMPLANTS, KITS AND METHODS FOR CORRECTING BONE DEFECTS," 61/802,228, filed on Mar. 15, 2013, entitled "MOSAIC IMPLANTS, KITS AND METHODS FOR CORRECTING BONE DEFECTS," and 61/826,489, filed on May 22, 2013, entitled "MOSAIC IMPLANTS, KITS AND METHODS FOR CORRECTING BONE DEFECTS." The entire disclosures of the foregoing provisional patent applications are incorporated by reference herein.

BACKGROUND

Bone tissue defects that cannot adequately heal via tissue regeneration often can be filled using autograph, allograph or synthetic scaffold materials. For large defects such as defects in the cranium or long bones, healing can be especially difficult. As a result, various scaffold strategies have been developed which utilize metal meshes or various porous ceramic materials that provide structural support for new tissue (e.g., bone). Many current strategies using metal mesh alone can be problematic due to low new bone formation and/or infections. Many currently used ceramic materials are mechanically weak and fragile, leading to a high risk of scaffold failure One advantage of metal meshes is that they often can be shaped to closely fit the defect. Ceramic scaffolds, on the other hand, typically cannot be shaped after manufacturing and therefore have to be custom made in advance. In an attempt to overcome the problem of low bone in-growth with metal meshes, coating the mesh with hydroxylapatite powder has been proposed, particularly for use in revision surgery in joint replacement.

A more recent approach is described in PCT Pub. No. WO 2011/112145 A1, titled Implants and Methods for Correcting Tissue Defects, published Sep. 15, 2011. The foregoing published application is incorporated herein by way of reference, and is hereinafter referred to as "the '145 App." The '145 App. describes mosaic implants which comprise a plurality of biocompatible mosaic plates which are connected by a wire (e.g., wire mesh) anchoring arrangement.

While a variety of devices and techniques may exist for correcting bone defects, it is believed that no one prior to the inventors has made or used an invention as described herein.

BRIEF DESCRIPTION OF THE DRAWINGS

While the specification concludes with claims that particularly point out and distinctly claim the invention, it is believed the present invention will be better understood from the following description of certain examples taken in conjunction with the accompanying drawings. In the drawings, like numerals represent like elements throughout the several views.

Figure 1:
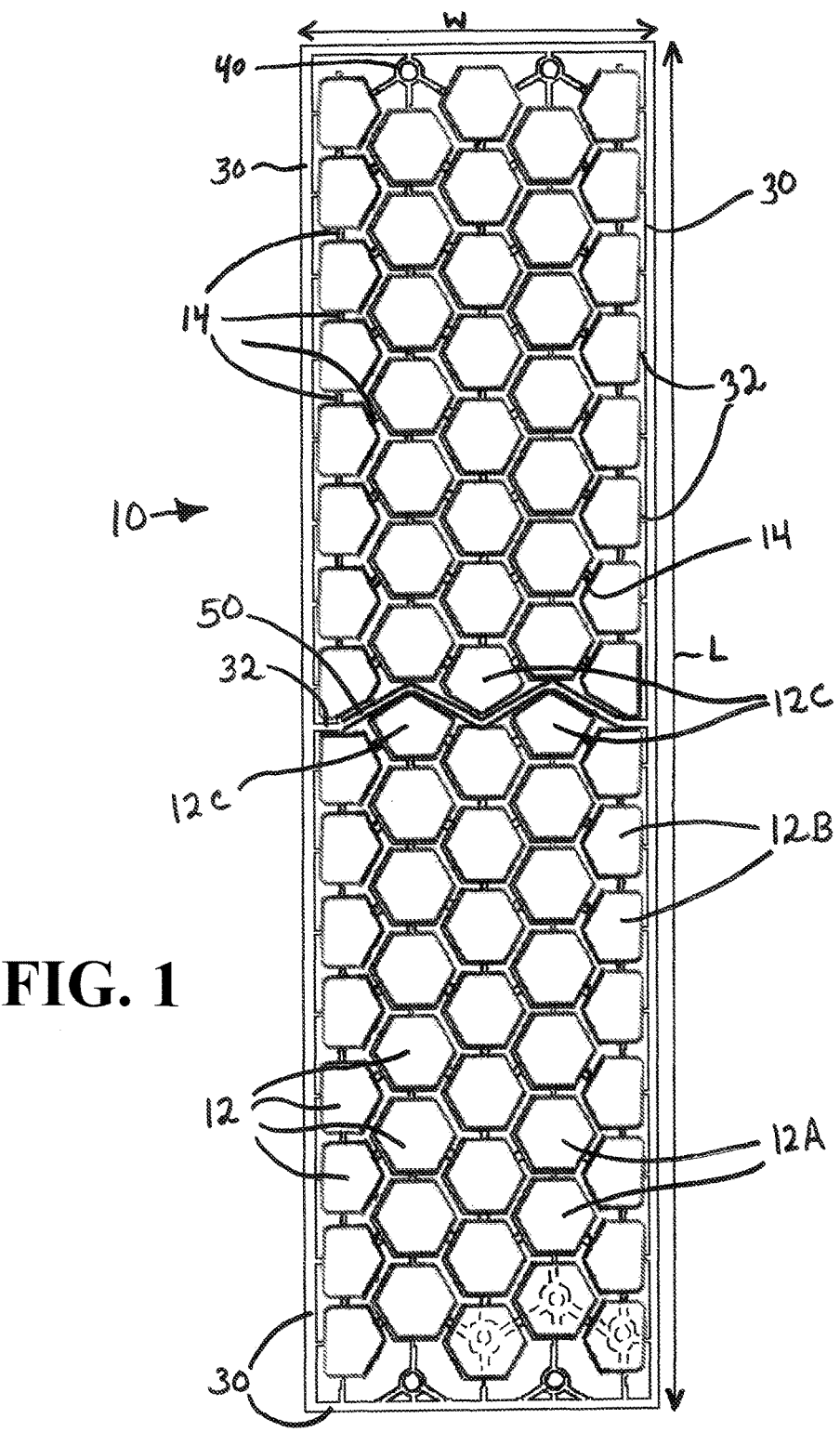
FIG. 1 depicts a top plan view of one embodiment of an implant section, as further described herein.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description. As will be realized, the versions described herein are capable of other different and obvious aspects, all without departing from the invention. Accordingly, the drawings and descriptions should be regarded as illustrative in nature and not restrictive.

Examples described herein relate to implants for use in correcting various bone defects, such as implants for use in cranioplasty procedures. The implants generally include a plurality of biocompatible mosaic plates that are interconnected with one another by a plurality of wires extending between adjacent plates. Embodiments of the implants described herein also include retention features such as a plurality of eyelets located about the periphery of the implant through which fasteners (e.g., bone screws) may be driven into bone surrounding a defect.

In some instances, the implants are configured such that the implant may be cut to various sizes while still providing the retention features about the periphery of the implant. In this manner, an implant comprising a plurality of biocompatible mosaic plates interconnected with one another by a plurality of wires extending between adjacent plates is fabricated in a predetermined configuration that is not specific to a defect in a particular patient. Thereafter, the implant is sized and shaped (e.g., deformed into a curved shape corresponding to the shape of the defect, and/or cut to size) according to the needs of a particular patient. Some embodiments provide two or more implants in predetermined configurations (e.g., two or more different sizes) such that one of the implants may be selected for use in a particular patient, and then sized and shaped as necessary.

In some embodiments, an implant ready for implantation in a patient comprises a single section of interconnected mosaic plates. In other embodiments, an implant comprises two or more implant sections that are coupled to one another in order to form an implant. By way of example, two implant sections are coupled to one another along a beam portion that extends across a length of the implant. In one particular example, two implant sections are coupled to one another along adjacent sides such that the beam portion is provided by the coupled sides of the implant sections. In still further embodiments, a series of implant sections, which may be identical or different in size, shape and/or configuration, are coupled together so as to form a single implant for use in a patient.

Implants described herein, whether comprising a single implant section or a plurality of implant sections coupled to one another, are also deformable such that at least a portion of the implant is conformable to a curved surface (e.g., a spherical, spheroidal, cylindrical, etc. surface). In this manner, for example, the implant may be deformed such that the upper and lower surfaces of the mosaic plates will form a generally curviplanar surface (with small gaps between adjacent plates). The implant may be shaped at the time of fabrication (e.g., after molding of the mosaic plates) and/or at another time prior to implantation in a patient (e.g., in an operating room).

When deformed in this manner, either at the time of fabrication or by a medical practitioner in the operating room, some embodiments described herein include additional components and/or features which provide structural support to the curved portion of the implant so as to resist deformation of the curved portion following implantation in a patient (e.g., due to external mechanical loads). In other words, the curved surface of the implant will not flatten or cave inward in response to external mechanical loads. In some embodiments, the beam portion of coupled implant sections provides such structural support. Alternatively, or in addition thereto, one or more support girders may also be provided on one or more of the implant sections and/or across an implant in order to provide similar structural support. By providing such structural support, implants described herein may be used to treat large defects. Multiple implant sections may be coupled together in any of a variety of combinations so as to allow the implant to not only conform to the desired shape (in terms of size, curvature and perimetral shape), but also span defects of considerable size. By way of example only, cranial defects (e.g., regions where a patient's cranium is missing) up to about 200 mm×about 130 mm in size, with the missing portion of the cranium having a variety of curvatures, may be treated using the implants described herein.

As used herein, the term "wire" refers to a strand, rod, strut, or similar structure having a length that is relatively long compared to its width and thickness, regardless of cross-sectional shape. For example, a "wire," as used herein, can have a circular, oval, rectangular, or other cross-sectional shape. In some of the embodiments described herein, some of the wires of the implants do not have a constant width and/or thickness along their entire length, and may have segments or regions that are irregular in shape. For example, some wires may have a pleated or crimped segment that allows the effective length of the wire to be elongated or shortened, while others have segments of reduced width and/or thickness to provide regions of greater flexibility. In other embodiments, one or more wires have segments of increased width and/or thickness in order provide greater rigidity and/or support to the implant. An individual wire may be in the form of a single, continuous structure, or a plurality of individual filaments or strands may be combined to form a wire (e.g., wrapped or braided).

The wires may be made from any of a variety of biocompatible materials suitable for implantation in a patient, such as various metals, polymers, or even composite materials of two or more metals and/or polymers. Non-limiting examples include biocompatible polymers such as polycaprolactone, shape memory alloys such as nitinol, titanium, titanium alloys (e.g. $Ti_6Al_4V$) and stainless steel. The wires may also be formed in any of a variety of manners such as forging, casting, molding, extrusion, cutting, etching, stamping, etc. In certain embodiments described further herein, the wires which interconnect the mosaic plates are formed from a metal sheet (e.g., titanium) which is stamped or cut (e.g., using an automated laser cutting device) in a predetermined pattern to produce a unitary mesh of connected wires having a wire rim extending about at least a portion of its periphery.

Figure 2:
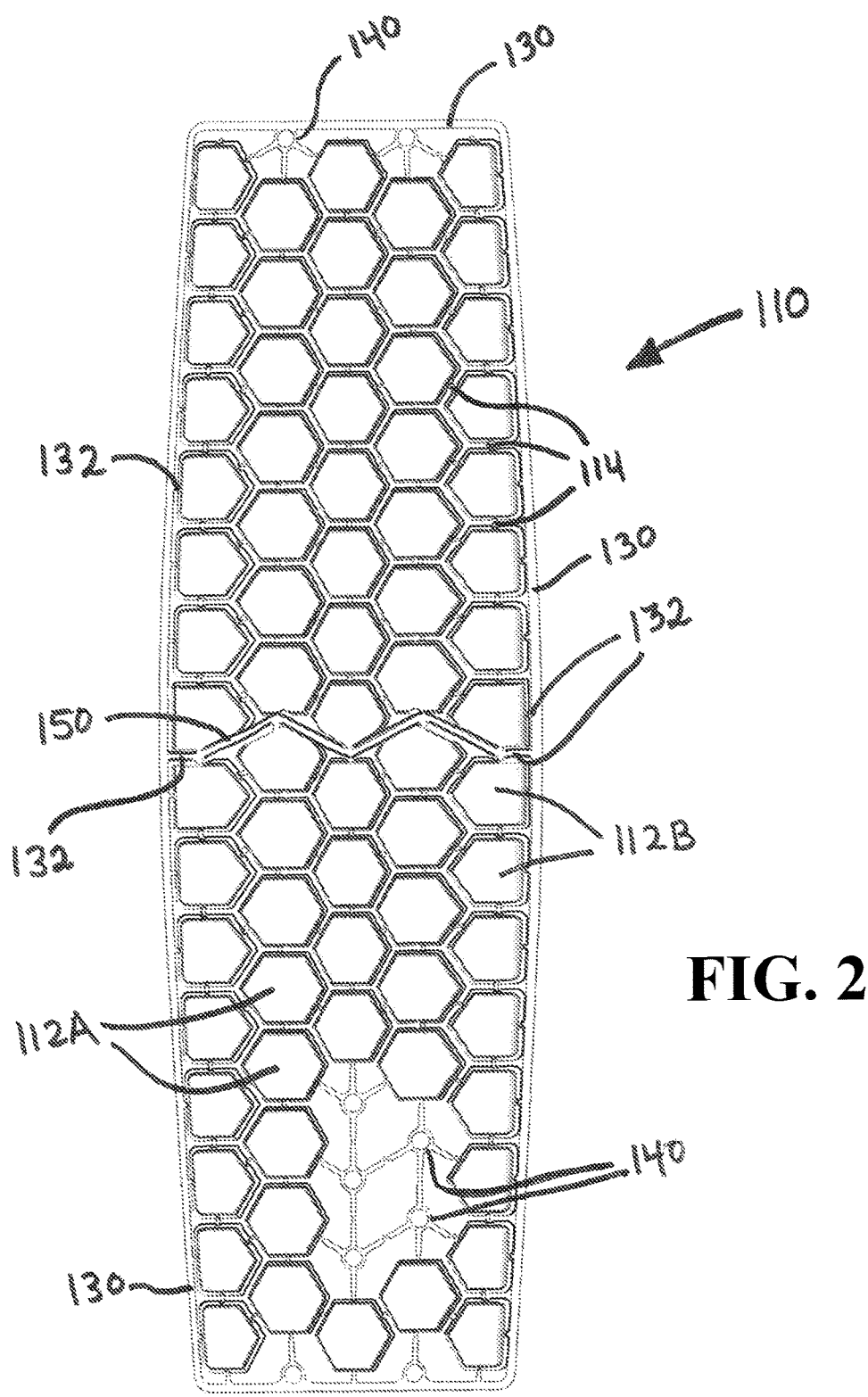
FIG. 2 depicts a top plan view of another embodiment of an implant section, with a portion of the mosaic plates removed in order to show additional aspects of the wire mesh support frame, and further wherein the implant section of FIG. 2 has tapered sides such that the width of the implant section is widest at its center.
Figure 3:
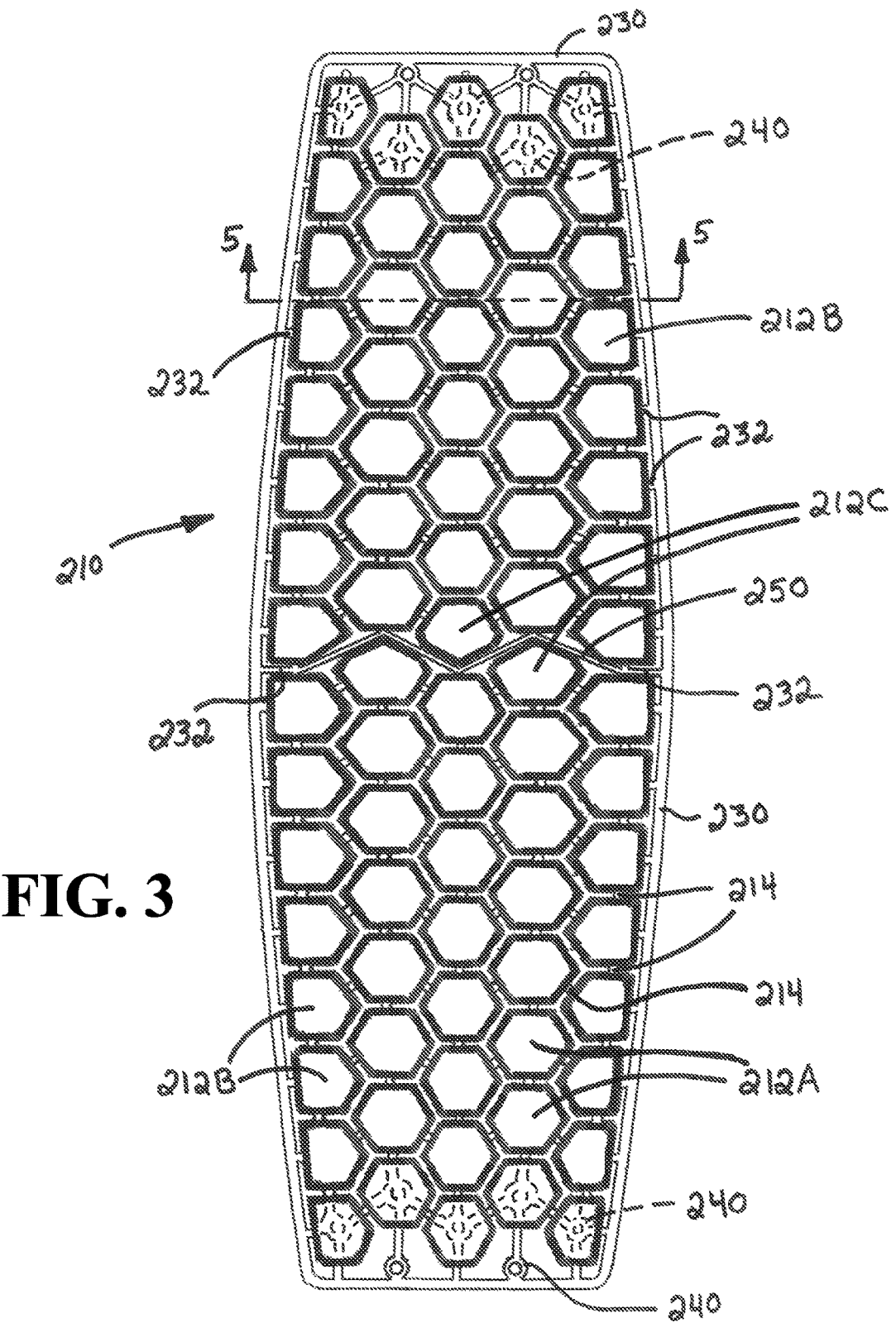
FIG. 3 depicts a top plan view of yet another embodiment of an implant section having further tapered sides compared to that of FIG. 2.

FIGS. 1-3 depict exemplary mosaic implant sections (10, 110, 210) which may be used either individually or in combination in the repair of bone and other tissue defects in mammals (including human patients). For example, two or more of mosaic implant sections (10, 110, 210), either identical sections or any combination of different sections, may be coupled together to provide a single implant. Any number of shapes and sizes of mosaic implant sections may be provided, and the three shown are merely exemplary of three possible configurations.

Whether used singly or in a combination of two or more implant sections coupled to one another, the resulting mosaic implant is conformable to various curved shapes in order to match that of a patient's bone defect. In one embodiment, by providing a plurality of differently shaped, sized and/or configured mosaic implant sections (10, 110, 210), such as in the form of a kit, two or more implant sections may be selected and coupled together to provide an implant which is sized and configured for a particular patient. For example, the resulting implant comprising two or more of mosaic implant sections (10, 110, 210) may be configured to match a particular patient's cranial defect in terms of size, shape (e.g., perimetral shape) and, in some instances, curvature. In other instances, a single implant section (10, 110, 210), optionally cut to size and shape as necessary, will be suitable for a relatively small defect in a patient. Larger defects can be treated with two or more implant sections (10, 110, 210) coupled together so as to provide an implant of a sufficient size for the patient's defect. As further described herein, some embodiments of coupled implant sections provide additional structural support and/or implants having a greater degree of curvature. Kits for such purposes are also described further herein.

Figure 4:
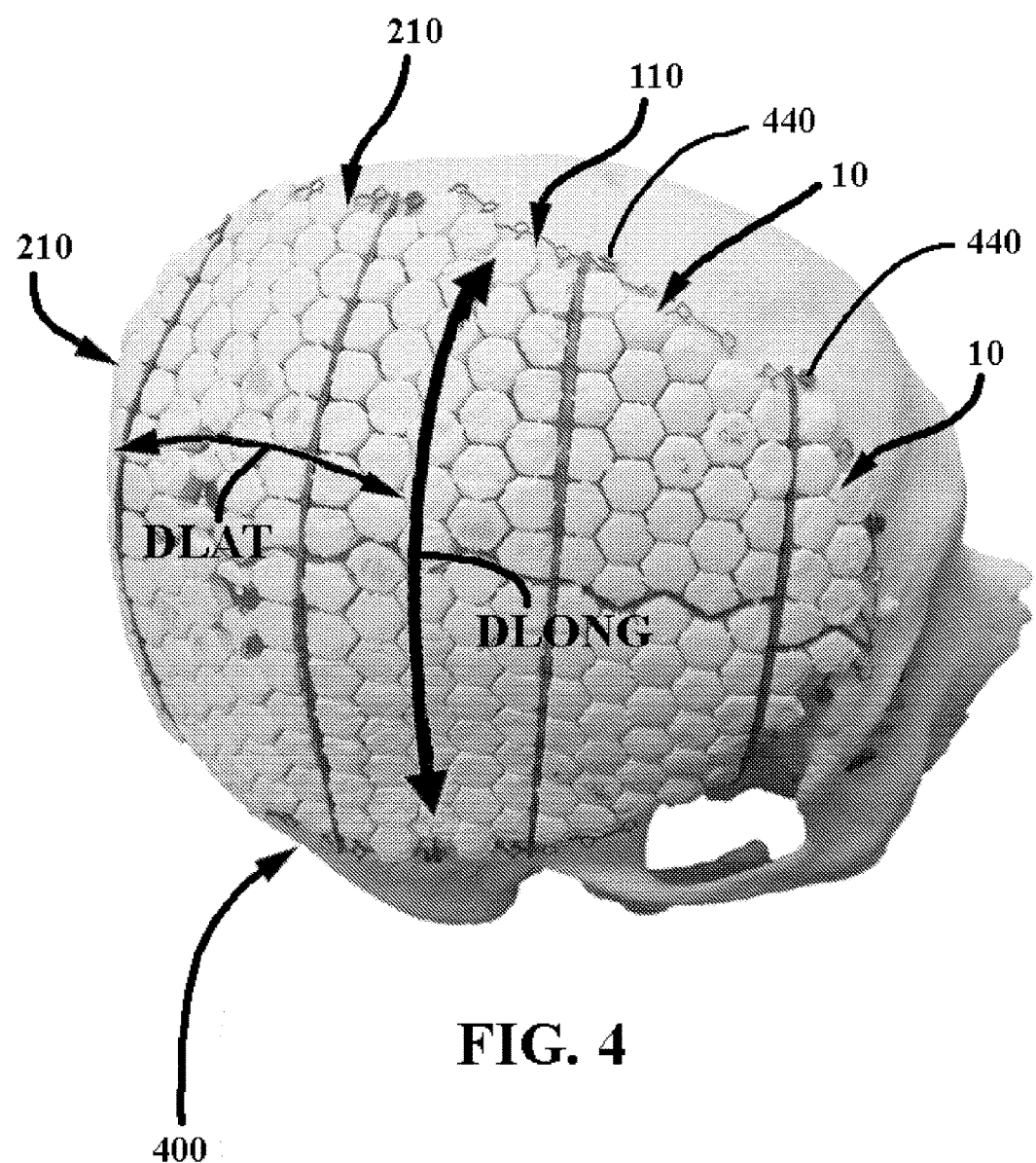
FIG. 4 shows an implant fabricated from the implant sections of FIGS. 1-3, simulating the implant secured to a patient's cranium over the area of a defect.

By way of one specific example, FIG. 4 depicts an exemplary mosaic implant (400) implanted in a skull having a very large defect. In this illustration, a large portion of the skull is missing as the result of, for example, trauma. Mosaic implant (400) comprises five implant sections that have been coupled together along their adjacent sides. Specifically, implant (400) comprises, from left to right, an implant section (210), another implant section (210), an implant section (110), and two implant sections (10). Each of the implant sections also has been trimmed in length, as further described herein. In addition, the far right implant section (10) also has been trimmed in width. In this manner, implant (400) is sized and shaped to correspond to the patient's bone defect.

As also seen in FIG. 4, implant (400) is shaped so that it generally conforms to a curved surface corresponding to the typical shape of the missing portion of patient's cranium. In other words, implant (400) has been shaped (i.e., deformed) to match the patient's cranial shape. Such shaping not only helps to ensure the maintenance of sufficient cranial volume upon bone in-growth and implant resorption, but also provides a cosmetically pleasing appearance. In addition and as further described herein, implant sections (10, 110, 210) are configured and coupled together such that implant (400) has high mechanical strength which, following implantation in a patient, resists deformation due to external mechanical loads. Implant (400), for example, will resist flattening or caving-in due to mechanical loads or impact which might occur during normal daily activities. Without one or more of the structural support features described further herein, implant (400) would be more likely to collapse or bend inwardly as a result of an external force applied against the area of implant (400).

Implant (400) can be attached to host tissue (e.g., the patient's cranial bone about the perimeter of a defect) via sutures, plates, screws, clamps and/or any of a variety of other fasteners or fixation devices. In FIG. 4, implant (400) is attached to the surrounding cranial bone using a plurality of screws (e.g., titanium bone screws) inserted through retention eyelets (40, 140, 240) located along portions of the periphery of the implant sections (10, 110, 210), as described further herein.

Returning to FIGS. 1-3, each implant section (10, 110, 210) comprises a plurality of biocompatible mosaic plates (12, 112, 212) which are interconnected with one another by a plurality of wires (14, 114, 214). Each mosaic plate (12, 112, 212) is connected to a plurality of the immediately adjacent mosaic plates by the wires (14, 114, 214). In general, each plate (12, 112, 212) (or at least a majority of the plates of an implant section) is connected to two or more adjacent plates by the wires (14, 114, 214). In the particular examples shown in FIGS. 1-3, the mosaic plates located along the side, top and bottom edges of the implant section are connected to two or three adjacent plates. In contrast, the interior mosaic plates are connected to four of the six adjacent plates. Also in the embodiments shown, wires (14, 114, 214) extend between and into the adjacent connected plates (12, 112, 212).

As further described herein, the wires (14, 114, 214) may be configured such that separate, non-intersecting, non-connected wires extend between adjacent plates. In other embodiments, wires (14, 114, 214) comprise an arrangement of crossing wires which may or may not be connected to each other, as described in the '145 App. In yet another embodiment, and as shown in FIGS. 1-3 and described below, wires (14, 114, 214) are integrally formed with one another such as by cutting (e.g., laser cutting), etching or stamping a flat sheet in order to provide wires (14, 114, 214) in the form of wire segments connected to one another via retention eyelets (40, 140, 240) so as to provide wire mesh. As used herein, a "mesh" comprises an arrangement of wires wherein at least two crossing wires are joined at one, some, or all of their intersections, or wherein wire segments (e.g., wires (14, 114, 214) are joined to one another (e.g., via eyelets (40, 140, 240) such that open regions are located between and bounded by adjacent wires. In the embodiments shown in FIGS. 6-8, the open regions between and bounded by adjacent wires (14, 114, 214) have the shape of a parallelogram. It will be understood, however, that any of a variety of other mesh arrangements may be employed.

Biocompatible mosaic plates (12, 112, 212) can be composed of any of a variety of resorbable and/or stable (i.e., non-resorbable) biocompatible materials, including various types and/or combinations of polymers, ceramics and metals. In some embodiments, the plates are composed of an osteoconductive and/or osteoinductive material. Osteoconductive materials serve as a scaffold on which bone cells will attach, migrate, and grow and divide so as to form new bone on the surfaces of the plates (12, 112, 212). Osteoinductive materials induce new bone formation around the plates (12, 112, 212). In the embodiments described herein, having the plates (12, 112, 212) arranged such that a gap is provided between adjacent plates, osteoconductive and/or osteoinductive mosaic plates will facilitate bone growth onto and between the plates of the implant (400), since the gaps allow for the free circulation of blood and tissue fluids between the plates.

In some embodiments, biocompatible mosaic plates (12, 112, 212) are composed of a moldable bioceramic or biopolymer material. While bioceramic materials can be produced by sintering ceramic powders, it can be difficult to produce complex shapes in this manner. Alternatively, bioceramics can be formed by a chemical bonding route whereby the ceramic material is formed by chemical reaction, such as a cement setting and hardening reaction.

In a particular embodiment, a hydraulic cement composition is used to mold mosaic plates (12, 112, 212). Non-limiting examples include cement precursor compositions comprising one or more Ca-salts such as calcium sulfates, calcium phosphates, calcium silicates, calcium carbonates and combinations thereof. As further described herein, the biocompatible plates are formed by molding the cement composition around portions of the wires (14, 114, 214). A powdered cement precursor composition is combined with either a non-aqueous water-miscible liquid or a mixture of water and a non-aqueous water-miscible liquid. The mixture is then poured or injected into a mold having the wires (14, 114, 214) positioned therein, and allowed to harden (e.g., in a water-containing bath) so as to form the mosaic plates (12, 112, 212) interconnected to one another by the plurality of wires (14, 114, 214).

Various cement compositions that may be used to mold mosaic plates (10, 110, 210) are described, for example, in U.S. Provisional Pat. App. No. 61/737,355, filed Dec. 14, 2012, titled "Cement-Forming Compositions, Cements, Implants and Methods for Correcting Bone Defects." Alternative cement compositions for use in molding the plates, including storage stable premixed hydraulic cement compositions, are described in PCT App. No. PCT/IB2012/054701, filed Sep. 10, 2012, titled "Storage Stable Premixed Hydraulic Cement Compositions, Cements, Methods, and Articles." Still further cement compositions which may be used to mold the plates (12, 112, 212) are described, for example, in the '145 App., as well as PCT App. No. PCT/IB2012/054228, filed Aug. 21, 2012, titled "Implants and Methods for Using the Implants to Fill Holes in Bone Tissue," and PCT Pub. No. WO 2010/055483 A2, published May 20, 2010, titled "Hydraulic Cements, Methods and Products." Each of the foregoing patent applications and publications is incorporated by reference herein.

In one embodiment, the compositions are calcium phosphate cement-forming compositions that comprise a monetite-forming calcium-based precursor powder and a non-aqueous water-miscible liquid.

In one specific embodiment, the monetite-forming calcium-based precursor powder comprises monocalcium phosphate (monocalcium phosphate monohydrate (MCPM) and/or anhydrous monocalcium phosphate (MCPA)) and β-tricalcium phosphate in a weight ratio of 40:60 to 60:40, and from 2 to 30 weight percent, based on the weight of the precursor powder, of dicalcium pyrophosphate powder (also referred to herein as calcium pyrophosphate). The powder to liquid (wt/vol) ratio in the composition is from 2 to 6 g/ml.

In another embodiment, the compositions are calcium phosphate cement-forming compositions that comprise a monetite-forming calcium-based precursor powder and are adapted to be mixed with an aqueous liquid or exposed to an aqueous liquid to achieve hardening. In one specific embodiment, the monetite-forming calcium-based precursor powder comprises monocalcium phosphate (monocalcium phosphate monohydrate (MCPM) and/or anhydrous monocalcium phosphate (MCPA)) and β-tricalcium phosphate in a weight ratio of 40:60 to 60:40, and from 2 to 30 weight percent, based on the weight of the precursor powder, of dicalcium pyrophosphate powder (also referred to herein as calcium pyrophosphate).

The molded plates (14, 114, 214) may thus comprise monetite and from 2 to 30 weight percent of dicalcium pyrophosphate. The monetite composition contains a majority of monetite, and in specific embodiments, contains at least 55 wt %, at least 60 wt %, at least 65 wt %, at least 70 wt %, at least 75 wt %, at least 80 wt %, at least 85 wt %, or at least 90 wt %, monetite. Such compositions results in slower implant resorption in a bone defect repair in a patient, as well as improved bone induction in a bone defect repair in a patient.

In additional embodiments, the monetite-forming calcium-based precursor powder comprises monocalcium phosphate and β-tricalcium phosphate mixed in a weight ratio of 45:55 to 52:48, and calcium pyrophosphate powder. In specific embodiments, the monocalcium phosphate (monocalcium phosphate monohydrate (MCPM) and/or anhydrous monocalcium phosphate (MCPA)) is acidic and has a pH of less than 6.0. In a more specific embodiment, a 0.1 g/ml saturated aqueous solution of the monocalcium phosphate has a pH less than 3.0. In a more specific embodiment, the MCPA and MCPM should exhibit a pH of 2.5-2.8. In one embodiment, the monocalcium phosphate (MCP) consists essentially of MCPA, whereby significant amounts of MCPM, i.e., greater than about 25%, or greater than about 10%, or greater than about 5%, based on the weight of the monocalcium phosphate, are excluded. In another embodiment, the monocalcium phosphate consists of MCPA. The MCPA does not contain any crystal water as is the case with mono calcium phosphate monohydrate.

In further embodiments, the calcium pyrophosphate (dicalcium pyrophosphate) comprises from 2 to 10 wt %, from 3 to 10 wt %, from 4 to 10 wt %, from 5 to 10 wt %, from 6 to 10 wt %, from 7 to 10 wt %, or from 8 to 10 wt %, of the precursor powder or the molded monetite composition. In further embodiments, the calcium pyrophosphate comprises from 2 to 5 wt %, from 3 to 5 wt %, or from 4 to 5 wt % of the precursor powder or the monetite composition. In still further embodiments, the calcium pyrophosphate comprises from 3 to 8 wt %, or from 4 to 7 wt % of the precursor powder or the monetite composition.

In further embodiments, the calcium pyrophosphate comprises from 2 to 15 wt %, from 3 to 15 wt %, from 4 to 15 wt %, from 5 to 15 wt %, from 6 to 15 wt %, from 7% to 15 wt %, from 8 to 15 wt %, from 9 to 15 wt %, from 10 to 15 wt %, from 11 to 15 wt %, or from 12 to 15 wt %, of the precursor powder or the monetite composition. In further embodiments, the calcium pyrophosphate comprises from 2 to 20 wt %, from 3 to 20 wt %, from 4 to 20 wt %, from 5 to 20 wt %, from 6 to 20 wt %, from 7 to 20 wt %, from 8 to 20 wt %, from 9 to 20 wt %, from 10 to 20 wt %, from 11 to 20 wt %, from 12 to 20 wt %, or from 15 to 20 wt %, of the precursor powder or the monetite composition. In further embodiments, the calcium pyrophosphate comprises from 2 to 25 wt %, from 3 to 25 wt %, from 4 to 25 wt %, from 5 to 25 wt %, from 6 to 25 wt %, from 7 to 25 wt %, from 8 to 25 wt %, from 9 to 25 wt %, from 10 to 25 wt %, from 11 to 25 wt %, from 12 to 25 wt %, from 13 to 25 wt %, from 14 to 25 wt %, from 15 to 25 wt %, or from 20 to 25 wt %, of the precursor powder or the monetite composition. In further embodiments, the calcium pyrophosphate comprises from 3 to 30 wt %, from 4 to 30 wt %, from 5 to 30 wt %, from 6 to 30 wt %, from 7 to 30 wt %, from 8 to 30 wt %, from 9 to 30 wt %, from 10 to 30 wt %, from 11 to 30 wt %, from 12 to 30 wt %, from 13 to 30 wt %, from 14 to 30 wt %, from 15 to 30 wt %, from 16 to 30 wt %, from 17 to 30 wt %, from 18 to 30 wt %, from 19 to 30 wt %, from 20 to 30 wt %, from 21 to 30 wt %, from 22 to 30 wt %, from 23 to 30 wt %, from 24 to 30 wt %, or from 25 to 30 wt %, of the precursor powder or the monetite composition.

In any of the embodiments disclosed herein, the calcium pyrophosphate may comprise alpha-dicalcium pyrophosphate, beta-dicalcium pyrophosphate and/or gamma-calcium pyrophosphate. In specific embodiments, the calcium pyrophosphate comprises beta-dicalcium pyrophosphate. In other specific embodiments, the calcium pyrophosphate comprises alpha-dicalcium pyrophosphate. In other specific embodiments, the calcium pyrophosphate comprises gamma-dicalcium pyrophosphate.

The precursor powder composition may comprise one or more additional Ca-salts selected from the group consisting of anhydrous dicalcium phosphate, dicalcium phosphate dehydrate (brushite), octacalcium phosphate, α-tricalcium phosphate, alpha-dicalcium pyrophosphate, gammadicalcium pyrophosphate, amorphous calcium phosphate, calcium-deficient hydroxyapatite, non-stoichiometric hydroxyapatite, tetracalcium phosphate, β-TCP granules, and/or combinations thereof, in minor amounts which do not change the monetite-forming quality of the precursor powder.

The porosity of the molded plates (12, 112, 212) may also be controlled, as the porosity affects bone in-growth and the resorption time in vivo. For example, porosity may be controlled by controlling monocalcium phosphate particle size in the precursor composition, and/or adding one or more porogens to the precursor composition. In some embodiments, the molded plates have a porosity of from 40 to 50%, and in other embodiments the porosity is about 46%.

In one specific embodiment, a monetite-forming precursor composition is used, and comprises: (a) acidic (pH<6) monocalcium phosphate (monocalcium phosphate monohydrate (MCPM) and/or anhydrous monocalcium phosphate (MCPA)); (b) β-tricalcium phosphate; and (c) 2-30 wt. % dicalcium pyrophosphate powder (also referred to as calcium pyrophosphate), based on the total weight of the precursor powder. The weight ratio of monocalcium phosphate to β-tricalcium phosphate is between 40:60 and 60:40. It will also be understood that the monocalcium phosphate portion of the precursor composition may include a small amount of monetite (e.g., 8-12%, based on the weight of the precursor powder).

The above-described combination of calcium phosphates (e.g., in the form of a powder mixture) is then mixed with a non-aqueous water-miscible liquid such as glycerol at a powder to liquid (g/ml) ratio of from 2 to 6. The liquid portion optionally may include up to 20% water (based on the total liquid volume). After mixing, the precursor mixture is injected into a mold having the wires (14, 114, 214) positioned therein, with portions of each wire extending into and between the mold cavities which are shaped to form the mosaic plates (12, 112, 212). The filled mold is then exposed to water, such as by placing the mold in a water bath, and the cement is allowed to harden (e.g., 24 hours in a room temperature water bath). The implant section (10, 110, 210) is then removed from the mold. Further processing such as soaking the implant section in water to remove glycerol residues may be performed, as necessary.

The thus-formed mosaic plates (12, 112, 212) in the example described above will comprise monetite ($CaHPO_4$) and 2-30 wt. % dicalcium pyrophosphate, along with varying amounts of other materials such as β-tricalcium phosphate and minor amounts of brushite ($CaHPO_4.2H_2O$) (e.g., less than 2 wt. % or less than 1 wt. %). The mosaic plates (12, 112, 212) in some embodiments comprise at least 65 wt %, at least 70%, at least 75%, at least 80%, at least 85%, or at least 90% monetite. As further discussed in U.S. Prov. Pat. Appl. 61/737,355, filed Dec. 14, 2012, the presence of dicalcium pyrophosphate not only delays resorption of the mosaic plates but also provides osteoinductivity (i.e., promotes new bone growth around and between the mosaic plates as compared to similar monetite formulations which do not include dicalcium pyrophosphate).

Each mosaic plate (12, 112, 212) may have any of a variety of shapes, such as triangles, circles, squares, rectangles, pentagons, hexagons, or other polygons. The shape of each plate may be regular (e.g., a pentagon or hexagon having sides of equal length) or irregular. The plates (12, 112, 212) of an implant section (10, 110, 210) may have the same or different shapes, regular and/or irregular. In some embodiments, the plates (12, 112, 212) have identical shapes (e.g., regular hexagons, squares or rectangles) and are arranged in a pattern such that each side edge of a plate is spaced apart from an edge of an immediately adjacent plate by the same (or nearly the same) amount so that a consistent gap is provided between adjacent plates. In other instances, there may be regions of the implant section (10, 110, 210) whereat the gap between adjacent plates is larger, for any of a variety of reasons (e.g., to accommodate a support structure). In the event that the mosaic plates of an implant section do not all have identical shapes, adjacent plates may nevertheless have complementary shapes such that the plates are arranged in a pattern with no overlap of plates and substantially equal gaps between adjacent plate edges.

In the specific embodiments shown in FIGS. 1-3, each implant section (10, 110, 210) includes both hexagonal (12A, 112A, 212A) and pentagonal plates (12B, 112B, 212B). The mosaic plates are arranged in five columns extending lengthwise along the length (L) of the implant section (10, 110, 210). The columns of plates are staggered such that consistent gaps are provided between the edges of adjacent plates, as shown. Thus, each column is shifted from an adjacent column in the lengthwise direction by slightly more than ½ the width of an individual plate.

The plates (12A, 112A, 212A) of the center three columns are in the shape of hexagons, each of approximately the same dimensions except for truncated plates (12C, 112C, 212C) located near the center of the implant section (10, 110, 210). Truncated plates (12C, 112C, 212C) are truncated along their edges adjacent a support girder (250) which extends across the width (W) of the implant sections (as discussed further herein). By truncating plates (12C, 112C, 212C), these plates do not cover support girder (250), thus allowing the implant section (10, 110, 210) to be deformed (curved) in the region of support girder (250) without fracturing plates (12C, 112C, 212C).

The plates (12B, 112B, 212B) in the outermost columns are in the shape of irregular pentagons. The outermost edges of plates (12B, 112B, 212B) (i.e., the edge adjacent the right and left sides of the implant sections) are aligned with one another in a linear (FIG. 1) or curvilinear (FIGS. 2 and 3) fashion. As described further herein, a wire rim (30, 130, 230) extends about the entire periphery of the implant section (10, 110, 210), and is connected to plates (12B, 112B, 212B) as well as support girder (50, 150, 250) via wire struts (32, 132, 232) which extend between the rim (30, 130, 230) and outer plates (12B, 112B, 212B) (as well as between the rim and the ends of the support girders). The outermost edges of pentagonal outer plates (12B, 112B, 212B) are aligned with, and spaced inwardly from, wire rim (30, 130, 230), as shown in FIGS. 1-3. In alternative embodiments, the wire rim (30, 130, 230) may extend about only a portion of the periphery of the implant section, such as along either side thereof.

On implant section (10), the right and left sides of rim (30), and hence the right and left sides of the implant section (10) are parallel such that implant section (10) has a rectangular shape. For implant sections (110, 210), on the other hand, the right and left sides of rim (130, 230) are curvilinear such that the implant section (110, 210) has the shape of a curved rectangle—the right and left sides are symmetrically curved, while the top and bottom ends are parallel. As a result implant sections (110, 210) are widest at their center (i.e., where support girder (150, 250) is joined to rim (130, 230), and symmetrically taper in width towards each end.

In alternative embodiments, the sides of an implant section may be linearly tapered rather than curvilinearly tapered. In such embodiments, are still widest at their center, but symmetrically taper in width towards each end along straight lines. As yet another alternative, only one side of an implant section may taper (linearly or curvilinearly). In still another alternative embodiment, one or both sides of an implant section may be tapered along only a portion of its length. For example, the sides of an implant section may taper in width from support girder (50, 150, 250) towards only the top or bottom ends.

Implant section (210) differs from implant section (110) in that implant section (210) is wider at support girder (250). In other words, the right and left sides of rim (230) of implant section (210) are more curved than the right and left sides of rim (130) of implant section (110). Additionally, in the depicted embodiments, implant sections (10, 110, 210) all have substantially the same width at their top and bottom ends. As will be discussed further herein, the varying configurations of implant sections (10, 110, 210) allow the implant sections to be coupled in a variety of arrangements in order to provide an implant (400) of a variety of different curvatures. Thus, any number of implant sections of additional shapes and configurations may be provided (e.g., one with sides having even greater curvature than implant section (210)) so as to enable additional combinations of implant sections for matching various bone defects.

Implant sections (10, 110, 210) may be provided in any of a variety of sizes. In the particular example shown, implant section (10) has a width W of about 39 mm and a length L of about 150 mm. Implant section (110) has a width of about 45 mm at its center (i.e., at support girder (150)) and 37 mm at the top and bottom ends, and a length of about 148 mm. Implant section (210) has a width of about 50 mm at its center (i.e., at support girder (150)) and 35 mm at the top and bottom ends, and a length of about 148 mm. Of course, these sizes are merely exemplary, as any of a wide variety of sizes and curvatures/tapers may be provided in the implant sections.

Figure 5:
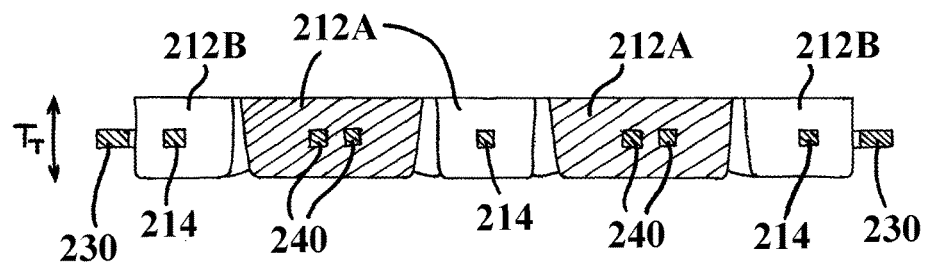
FIG. 5 depicts a cross-sectional view of the implant section of FIG. 3, taken along the line 5-5 thereof.

Mosaic plates (12, 112, 212) may be provided in any of a variety of sizes. By way of example only, mosaic plates (12A, 112A, 212A) shown in FIGS. 1-3 have a width ($W_T$) of approximately 8 mm at their bottom surface and approximately 8.4 mm at their top surface, wherein the plate width is defined as the distance between opposite, parallel sides of a plate. Thus, the sidewalls of the mosaic plates (12A, 112A, 212A) are sloped or tapered such that the plates are wider at their top surface than at their bottom surface (e.g., as depicted in FIG. 5). The thickness of mosaic plates (12A, 112A, 212A) is approximately 4 mm (as depicted by distance $T_T$ in FIG. 5). In addition, the gap between adjacent edges of plates (12, 112, 212) at the bottom surface of the plates is approximately 1 mm, and approximately 0.6 mm at the top surface. For implant section (210), on the other hand, the mosaic plates (212A), particularly those of the first and third columns, have varying sizes such that the plates (212A) at the ends of the implant section have a width of approximately 7.5 mm at their bottom surface and approximately 7.9 mm at their top surface. The plates (212A) at the middle of implant section (210) have a width of approximately 8.7 mm at their bottom surface and approximately 9.1 mm at their top surface. Of course, these dimensions are merely exemplary of one embodiment, as any of a variety of plate sizes and spacings may be used.

As also seen in the cross-sectional view of FIG. 5, the sidewalls of the mosaic plates may be sloped or tapered such that the plates are wider at their top surface than at their bottom surface. Alternatively, this sloping or tapering may be configured in a variety of other manners, such as tapering the sidewalls of the mosaic plates from both the top and bottom surfaces so that the plates are widest in cross-section across the center of the plate, or at some other location between the top and bottom surfaces. The sloping or tapering of the sidewalls allows the implant section to be deformed into various curvatures, with a deeper concavity in the bottom surface of the implant without the edges of adjacent mosaic plates coming into contact with each other than would be possible with vertical, non-tapered sidewalls.

In still other embodiments, the top surface width $W_T$ of each plate is between 2 and 20 mm, between 3 and 15 mm, or between 4 and 10 mm. In further embodiments, the mosaic plates have a thickness $T_T$ which is between 10% and 150% of $W_T$, between 20% and 80% of $W_T$, or between 30% and 60% of $W_T$. In order to obtain good aesthetical results, the thickness $T_T$ is as small as possible while maintaining sufficient strength of the plates. In adjusting an implant to a specific defect the thickness $T_T$ can be reduced by polishing or other material removal process, particularly along the periphery of the implant in order to improve implant fit and improve aesthetics (e.g., to provide a smooth, reduced height transition between the surface of surrounding bone and the upper surface of the implant).

In further embodiments, the gap between adjacent edges of plates at the bottom surface of the plates is less than 3 mm, less than 2 mm, or less than 1.2 mm. A smaller gap facilitates the filling of the gap by new bone growth. On the other hand, a smaller gap will inhibit the amount of deformation (i.e., curvature) which is possible when matching the implant to a patient's defect. In other words, having a larger gap allows the implant to be deformed more before adjacent plates contact each other, but larger gaps between plates also take a longer time to fill with new bone growth. It is of course possible to have different sized gaps between cavities if the implant is intended to have regions which will be substantially flat and other regions which will be deformed into various curvatures and shapes.

As mentioned previously, wire rim (30, 130, 230) which extends about the periphery of implant sections (10, 110, 210) is connected to plates (12B, 112B, 212B) as well as support girder (50, 150, 250) via wire struts (32, 132, 232). In addition, mosaic plates (12, 112, 212) are interconnected with one another by a plurality of wires (14, 114, 214) which extend between adjacent plates. In the embodiments shown, a single wire extends between each connected pair of adjacent plates. In other embodiments, two or more wires may extend between each connected pair of adjacent plates, as shown and described in the '145 App. Wires (14, 114, 214) may comprise separate, non-intersecting, non-connected wires which extend between and into adjacent plates—i.e., as individual wire segments. Alternatively, wires (14, 114, 214) may comprise crossing wires which may or may not be connected to each other, as described in the '145 App. In such arrangements, each wire may extend from one side or end of the implant section to the opposite side or end, such that each wire interconnects multiple pairs of adjacent plates.

Figure 6:
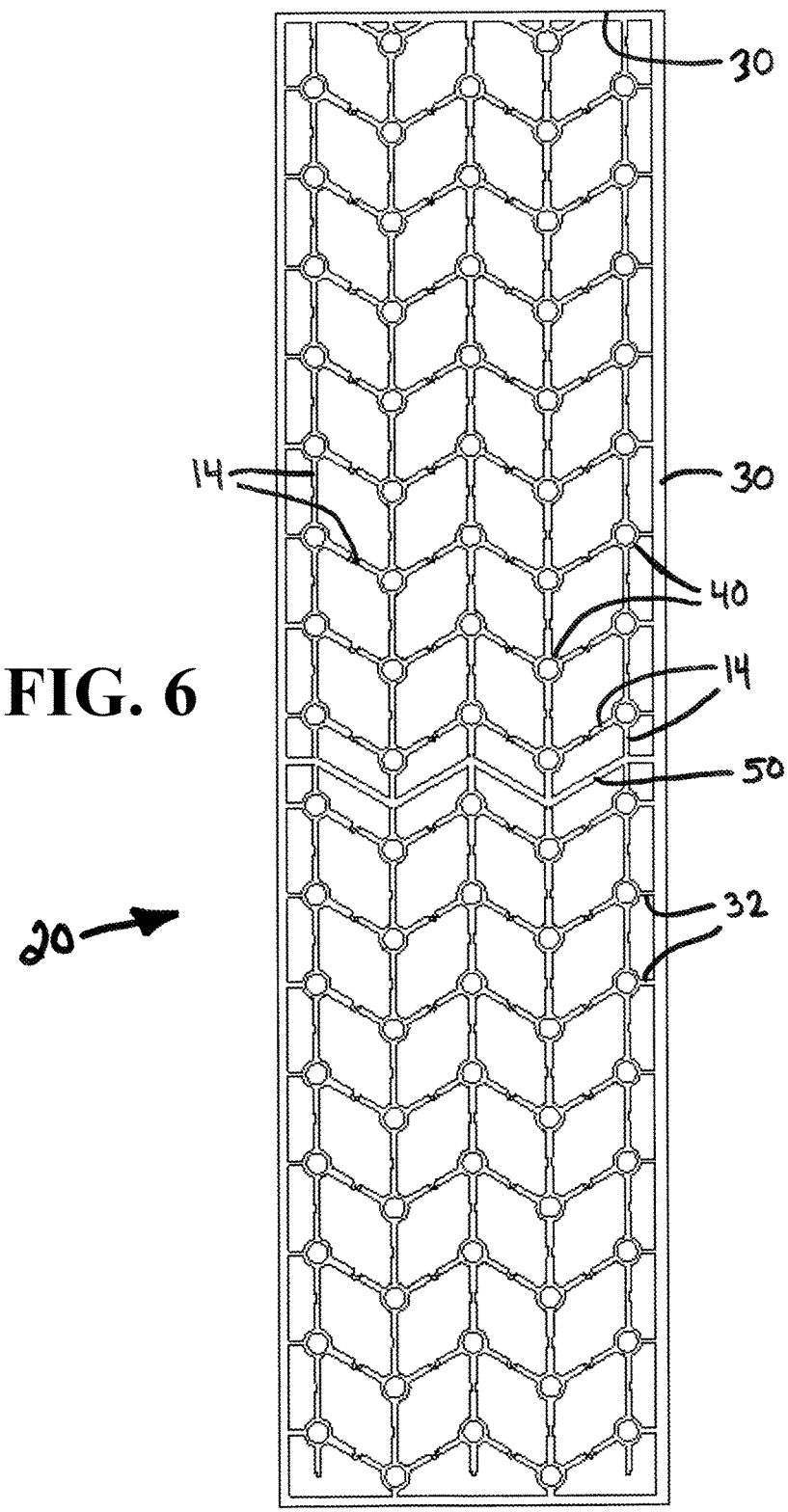
FIG. 6 is a top plan view of the wire mesh support frame of the implant section shown in FIG. 1.
Figure 7:
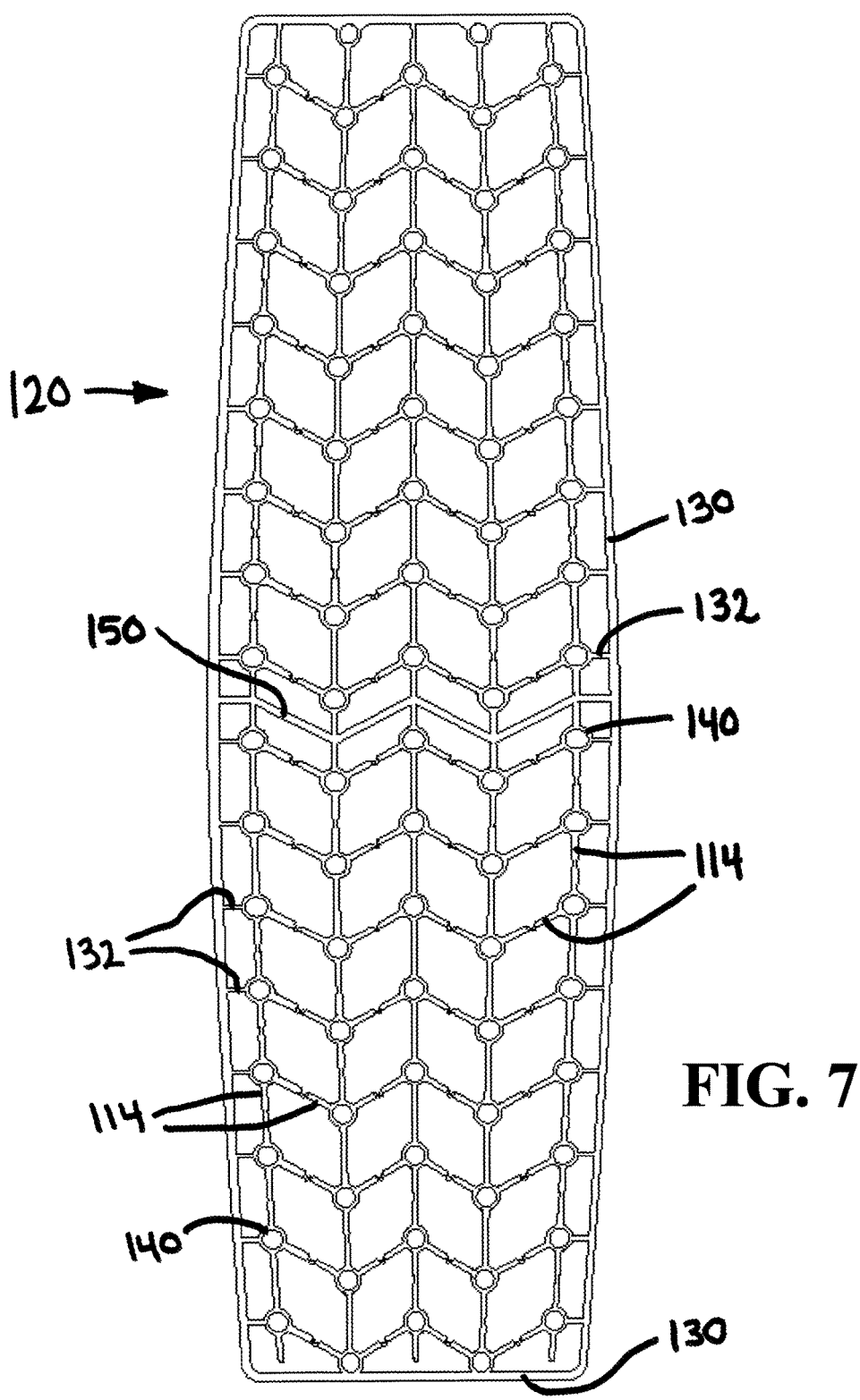
FIG. 7 is a top plan view of the wire mesh support frame of the implant section shown in FIG. 2.
Figure 8:
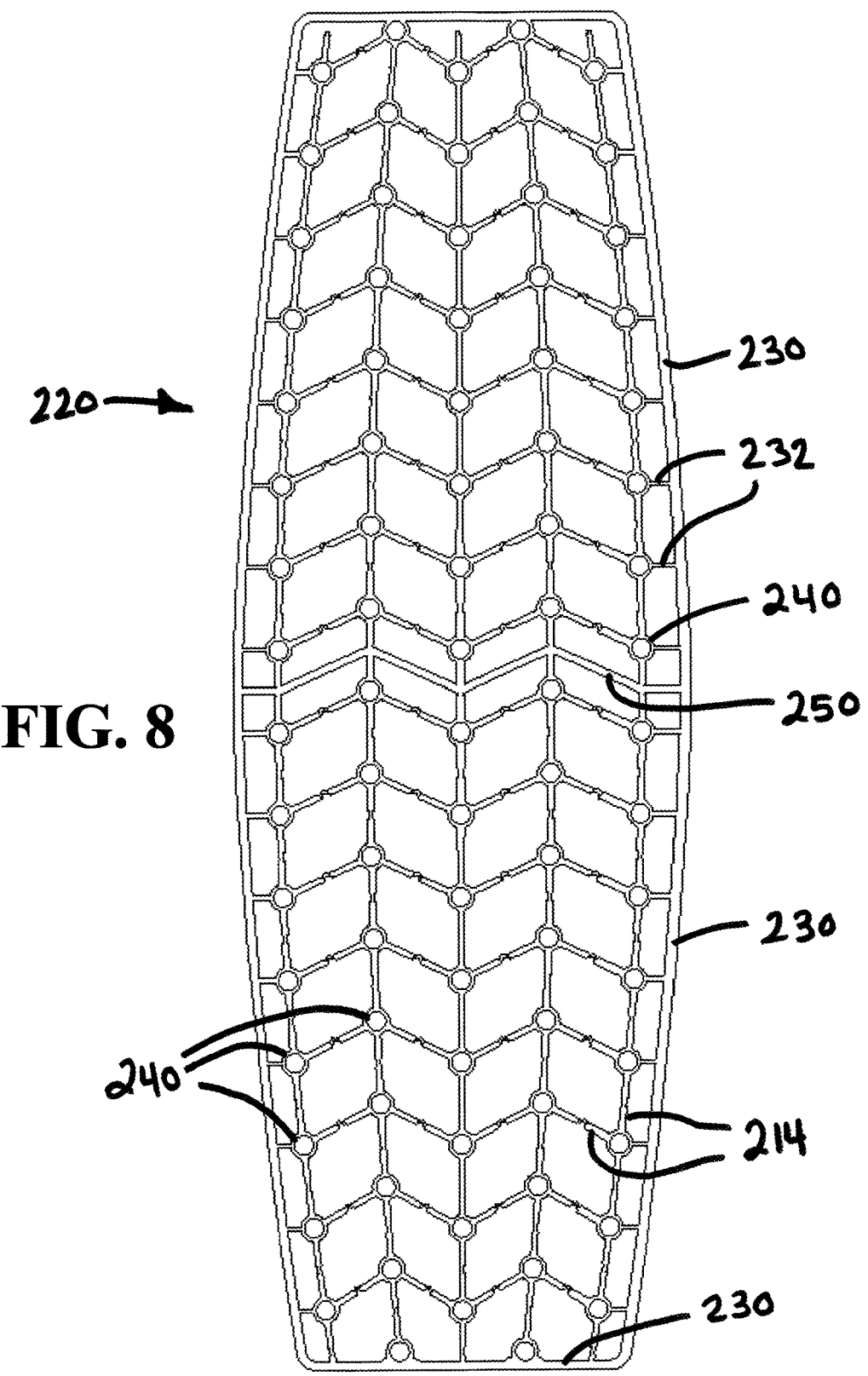
FIG. 8 is a top plan view of the wire mesh support frame of the implant section shown in FIG. 3.

In the embodiment shown in FIGS. 1-7, wires (14, 114, 214) are interconnected with one another via retention eyelets (40, 140, 240), some of which are also connected to rim (30, 130, 230) by wire struts (32, 132, 232). The resulting structure is a wire mesh support frame (20, 120, 220) which is bounded about at least a portion of its periphery by rim (30, 130, 230), as shown in FIGS. 6-8. Support frame (20, 120, 220) may be formed in a variety of ways such as by welding wire segments and eyelets to one another in the arrangement shown, or by a molding process. In the embodiments shown in FIGS. 6-8, the components of support frames (20, 120, 220) are integrally formed with one another by cutting (e.g., laser cutting), etching or stamping a flat sheet to form wires (14, 114, 214), eyelets (40, 140, 240), wire struts (32, 132, 232), support girder (50, 150, 250) and rim (30, 130, 230) from a single sheet of material. Any of a variety of materials may be used for support frames (20, 120, 220), such as biocompatible metals, including alloys. In the embodiments shown, support frames (20, 120, 220) are laser cut, using an automated, programmable laser cutting device, from a sheet of titanium. The titanium sheet comprises grade 2, 4 or 5 titanium, 0.3-0.6 mm thick. In the embodiment shown, grade 2 titanium, 0.4 mm thick is used. Alternatively, support frame (20, 120, 220) may be cut, etched, stamped, molded or otherwise formed from a biodegradable polymer such as polycaprolactone.

It should be noted that, as used herein, the term "eyelet" means an opening having a substantially closed perimeter, but it is not limited to a particular shape. Thus, eyelets (40, 140, 240) can be round, square, rectangular, trapezoidal, hexagonal, tear-drop, oval, elliptical or any other suitable shape. Of course, other types of attachment apertures or other fastening points may be used in place of, or in addition to the eyelets (40, 140, 240).

In the particular embodiments shown in FIGS. 1-3, each mosaic plate (12, 112, 212) is connected to a plurality of the immediately adjacent mosaic plates by the wires (14, 114, 214). Except for those located along the top and bottom ends of the implant section, the interior plates (12A, 112A, 212A) of the center three columns of plates are connected to four of the six adjacent plates. The plates (12A, 112A, 212A) of the center three columns located along the top and bottom ends are connected to three of the five adjacent plates. Similarly, except for those located along the top and bottom ends of the implant section, the plates (12B, 112B, 212B) in the outermost columns are connected to three of four adjacent plates. Finally, the plates (12B, 112B, 212B) of the outermost columns located along the top and bottom ends are connected to two of the three adjacent plates.

Figure 9:
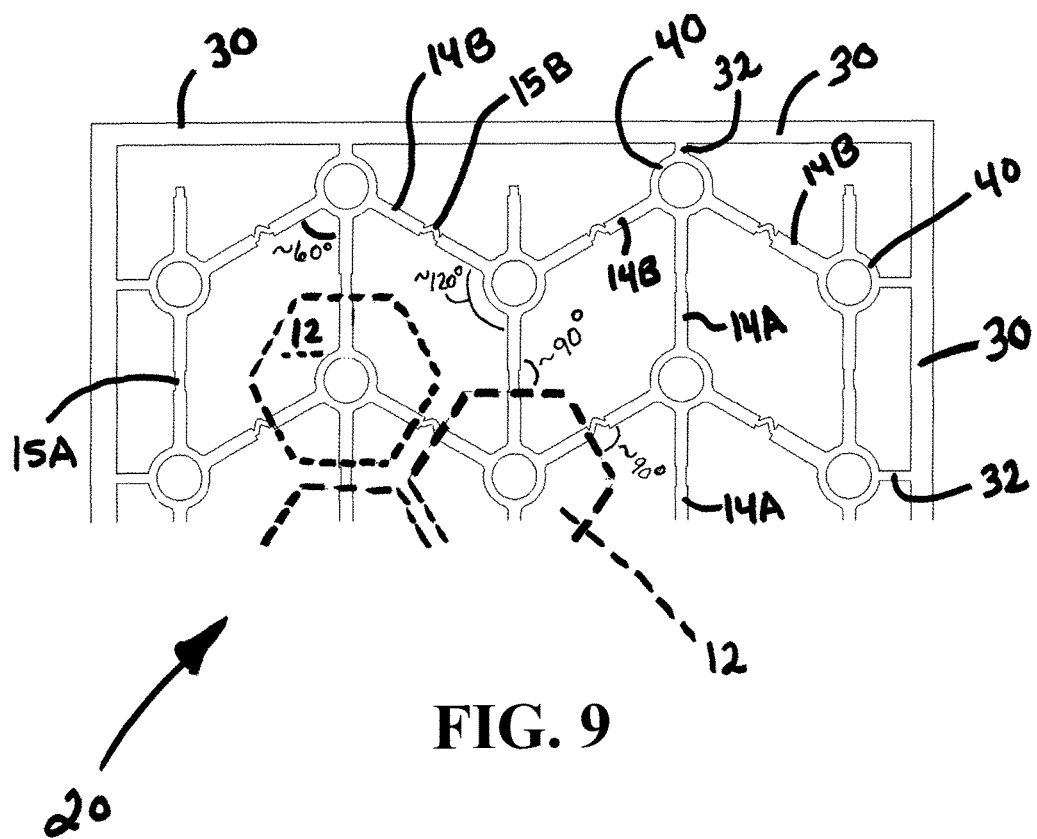
FIG. 9 depicts an enlarged view of a portion of the wire mesh support frame of FIG. 6.

Each eyelet (40, 140, 240) is positioned so as to be located entirely within the interior of a plate (12, 112, 212), such as approximately in the middle of the plate. In order to provide sufficient strength while also allowing the implant sections to be deformed (i.e., bent, particularly into various curvatures), wires (14, 114, 214) extend away from eyelets (40, 140, 240) so as to span between the adjacent, parallel sides of adjacent plates. Thus, wires (14, 114, 214) intersect the sides of the plates at an angle of approximately 90°, as best seen in FIG. 9.

In the particular arrangements of plates shown in FIGS. 1-9, vertical wires (14A, 114A, 214A) extend approximately parallel to the sides of the implant sections, in five straight or slightly curved columns. In implant section (10), wires (14A) extend in five parallel columns that are also parallel to the left and right sides of implant section (10). In implant sections (110, 210), the center column of wires (114A, 214A) extend parallel to the left and right sides of implant section (110, 210), while the other columns of wires (114A, 214A) are slightly curved to approximately match the curved sides of these implant sections (110, 210), the outermost columns of wires (114A, 214A) are slightly more curved than the columns spaced inwardly therefrom, but slightly less than the curvature of rim (130, 230) along the right and left sides of the implant sections (110, 210). Thus, wire struts (132, 232) of implant sections (110, 210) increase slightly in length progressing from the top and bottom ends towards support girder (150, 250).

The wires (14B, 114B, 214B) are arranged in a zigzag fashion across the width of the implant section (10, 110, 210), as shown. Thus, each wire (14B, 114B, 214B) extends from an eyelet (40, 140, 240) at an included angle of about 60° to one adjacent wire (14A, 114A, 214A) extending from the same eyelet, and at an included angle of about 120° to the other adjacent wire (14A, 114A, 214A) extending from the same eyelet. Each eyelet (40, 140, 240) therefore has four wires extending therefrom, either in the form of wires (14, 114, 214) or wires (14, 114, 214) in combination with wire struts (32, 132, 232).

When the support frame (20, 120, 220) is fabricated from a single sheet of metal, the wires (14, 114, 214), struts (32, 132, 232), eyelets (40, 140, 240), and rim (30, 130, 230) will generally have the same thickness. In the examples shown, the support frame members have a thickness of about 0.4 mm. The rim (30, 130, 230) has a width of 0.4 to 1.6 mm, or from 0.6 to 1.2 mm, or 1.0 to 1.2 mm. Wires (14, 114, 214) have a width of 0.4 to 0.6 mm, wire struts (32, 132, 232) have a width of about 0.45 mm, the interior diameter of eyelets (40, 140, 240) is approximately 2.1 mm, and the width of the metal forming the eyelets is about 0.4 mm.

In order to provide additional shapability to implant sections (10, 110, 210) and an assembled implant (400), the wires (14, 114, 214) include deformation zones. The deformation zones are generally located in the middle of the length of a wire (14, 114, 214) such that they will generally be positioned between adjacent plates so that deformation will occur between the plates so as to prevent cracking of the plates upon deformation of the implant section.

In the embodiments shown, wires (14, 114, 214) include two different types of deformation zones. Wires (14A, 114A, 214A) have reduced-width regions (15A, 115A, 215A) which are located between adjacent plates following molding. When the implant section is longitudinally deformed (i.e., curved about an axis which extends transverse to length L, as indicated by $D_{LONG}$ in FIG. 4), wires (14A, 114A, 214A) will deform (i.e., bend) at reduced-width regions (15A, 115A, 215A) so that such deformation is less likely to cause the plates to crack. By way of one example, when wires (14A, 114A, 214A) have a width of 0.5 to 0.7 mm, reduced-width regions (15A, 115A, 215A) have a width of 0.3 to 0.5 mm. It should be understood that "transverse" is not intended to mean at an angle of 90 degrees.

Also in the embodiments shown, wires (14B, 114B, 214B) have pleated regions (15B, 115B, 215B) which are also located between adjacent plates following molding. Pleated regions (15B, 115B, 215B) not only have a reduced width, they also include one or more pleats which allow additional deformation of the implant while avoiding cracking the plates. In particular, pleated regions (15B, 115B, 215B) facilitate lateral deformation of the implant section (i.e., curving the implant section about an axis which extends transverse to width W, as indicated by $D_{LAT}$ in FIG. 4). Wires (14B, 114B, 214B) will deform (i.e., bend) at pleated regions (15B 115B, 215B) rather than within the plates in order to avoid plate cracking. In addition, pleated regions (15B 115B, 215B) also allow the implant section to be locally stretched or compressed at pleated regions (15B 115B, 215B) in order to further facilitate shaping of the implant to match a patient's defect. In some instances, pleated regions (15B 115B, 215B) also allow for some adjustment of the retention eyelets (40, 140, 240) located along the top and bottom edges of the implant so as to properly locate these eyelets with respect to the bone surrounding a defect. In this manner, the eyelets can be repositioned somewhat to ensure that a screw or other fastener driven therethrough in to the surrounding bone will have sufficient purchase.

It should also be pointed out that although rim (30, 130, 230) generally can only be deformed along its length, struts (32, 132, 232) are deformable along their length. Thus, when an implant section is laterally deformed (as indicated by $D_{LAT}$ in FIG. 4), struts (32, 132, 232), portions of which are not located within the plates, will deform along their lengths in order to further facilitate matching the implant to a desired curvature. Support girder (50, 150, 250) is deformable in a similar fashion.

When two or implant sections (10, 110, 210) are needed in order to provide an implant (400) corresponding to the shape of a patient's defect, two or more implant sections may be coupled to one another along portions of their rims (30, 130, 230). Such coupling may be accomplished in any or variety of ways, such as using mechanical fasteners, biocompatible adhesives, welding, binding, etc. In the embodiments shown in FIGS. 4 and 10, the implant sections are coupled to one another by spot welding. Thus, the rims (30, 130, 230) extending along the sides of adjacent implant sections (10, 110, 210) are positioned in overlapping arrangement and then welded to one another at spot welds (431) along the length of the overlapping rims.

While the deformation of an implant section in either the $D_{LONG}$ or $D_{LAT}$ directions is limited only by the spacing between adjacent plates and the amount of sidewall tapering of the plates, deformation in both the $D_{LONG}$ and $D_{LAT}$ directions is much more limited unless plates are removed. This is a result of the fact that spheres, spheroids and other similarly curved surfaces are not developable. (A "develop-able surface" is one that that can be flattened onto a plane without the need for any stretching or compression.) One advantage of implant sections (110, 210) which have curved rims (130, 230) along their sides is that the implant sections may be attached to one another (or to implant section (10)) along with adjacent sides to provide a shape which more closely matches a non-developable curved surface, much that way that various map projections are used to approximate the curvature of the earth in a flat plane. Thus, when the rim (130) of an implant section (110) is coupled along its length to the rim (230) of an implant section (210), the implant section will be, and in fact must be, deformed in both the $D_{LONG}$ and $D_{LAT}$ directions, as seen in FIG. 4. Most of the curvature in the $D_{LAT}$ direction will result from deformation (i.e., bending of the struts (132, 232)), but this still allows implant (400) to be deformed so that the implant (400) is more conformable to a curved surface such as a sphere or spheroid or similar shapes corresponding to various regions of a cranium.

In addition, when rims (30, 130, 230) of implant sections (10, 110, 210) are coupled to one another, particular when done in an overlapping fashion, the rims of adjacent implant sections provide a beam portion extends across the length of the implant. This beam portion provides additional structural support to the curved implant (400) which resists deformation (e.g., flattening of the curved shape) following implantation in a patient. Similarly, support girder (50, 150, 250) also provides additional structural support across the central region of implant (400), often the most vulnerable area in terms of inward deformation (i.e., flattening or caving-in).

It will be understood that additional structural supports may be provided such as additional support girders extending across the width of an implant section. Similarly, the beam portion extending across a length of the implant may be provided in various alternative ways besides adjoining rims extending along the sides of coupled implant sections. For example, rim (30, 130, 230) itself provides structural support that resists inward deformation of a single implant section (10, 110, 210) which is implanted in a patient. Alternatively, one or more support girders similar to support girder (50, 150, 250) may be provided in the lengthwise direction, particularly in an arrangement wherein the support girder(s) is positioned in a zigzag arrangement between adjacent plates. Of course, additional support girders extending across the implant sections may also be provided at various desired locations. As yet another alternative, a separate support girder may be provided, with implant sections coupled to the support girder along either side thereof.

Figure 11:
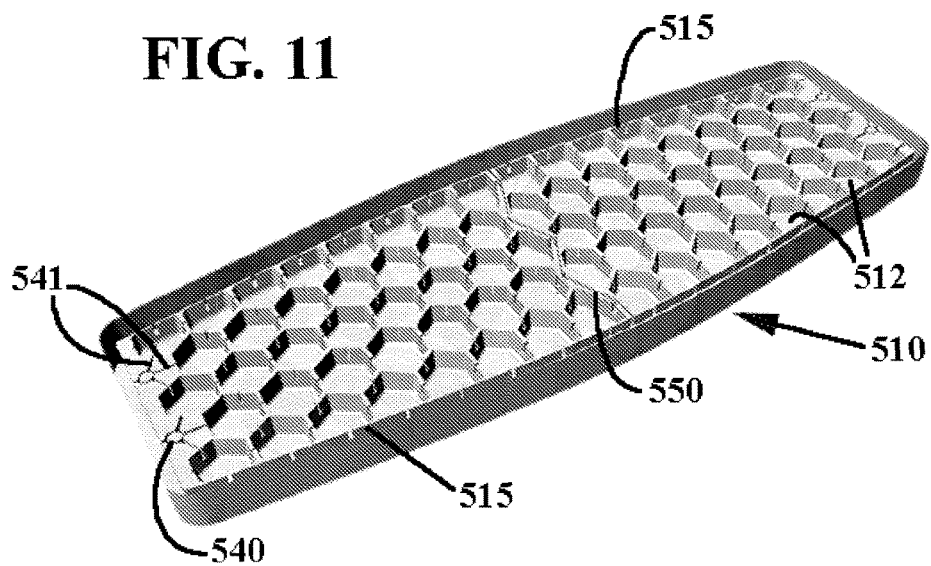
FIG. 11 depicts a perspective view of a mold suitable for forming the implant section of FIG. 3.
Figure 12:
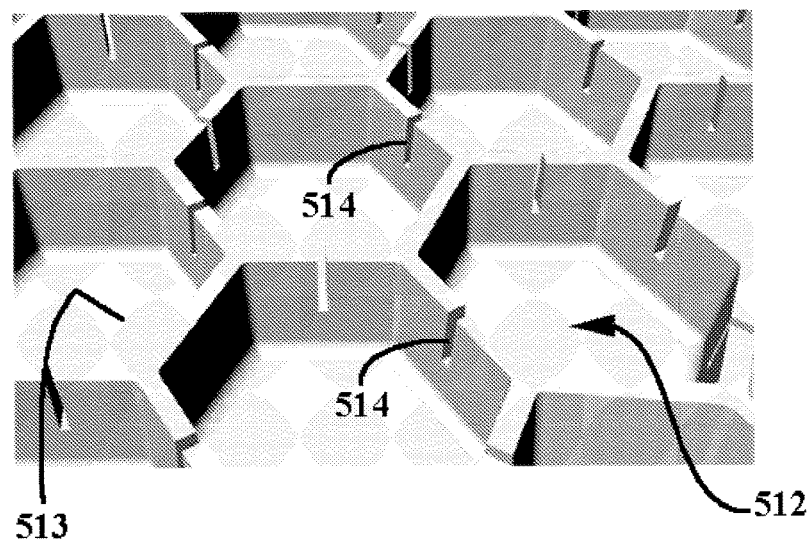
FIG. 12 depicts an enlarged view of a portion of the mold of FIG. 11.

As mentioned previously, implant sections (10, 110, 210) may be formed by a variety of processes, such as molding. In the specific embodiments shown, implant sections (10, 110, 210) are formed by molding plates (12, 112, 212) about the wires (14, 114, 214) of a support frame (20, 120, 220). One such mold (510) is shown in FIGS. 11 and 12, wherein the mold (510) is configured for use in forming implant section (210). Mold (510) may be formed of any of a variety of materials such as silicone, Teflon, other polymers or metals. Mold (510) includes a plurality of cavities (512) shaped and arranged for forming mosaic plates (212). Thus, cavities (512) have tapered sidewalls corresponding to the tapered sidewalls of the plates, as shown in FIG. 5. The bottom (513) of each cavity (512) corresponds to the bottom surface of a plate (212).

Channels (514) are provided in the sidewalls of selected cavities (513). Cavities (514) correspond to the locations of wires (214) of support frame (220) and have depth corresponding to the desired depth of the wires (214) in the implant section (210). Thus, channels (514) receive wires (214) therein. Circular cutouts (540) are also provided at the top and bottom ends of the mold to accommodate the eyelets (240) of support frame (220) which are not to be enclosed by plates (212), along with elongate grooves (541) which extend from cutouts (540) to the adjacent cavities (512). Elongate grooves (541) accommodate the wires (214) which extend away from eyelets (240). Similar, groove (550) extends across the width of the mold (510) for accommodating support girder (250) therein.

Prior to molding, a support frame (220) is positioned within mold (510) such that rim (230) extends about outer wall (515) of the mold cavities (512), with wires (214) positioned at the bottom of channels (514) and eyelets positioned within cutouts (540). The positioning of the wires (214) of support frame (220) is controlled by the depth of cutouts (540). Next, the precursor cement composition described previously (or other moldable composition) is inserted into the mold cavities (512) such as by pouring or injecting. While mold (510) does not require a top plate, other embodiments of mold (510) may include a top plate for enclosing the mold either before or after addition of the precursor composition. If the mold is sealed prior to the addition of the cement composition, the mold will include one or more sprues through which the cement may be injected into the mold cavities.

Figure 10:
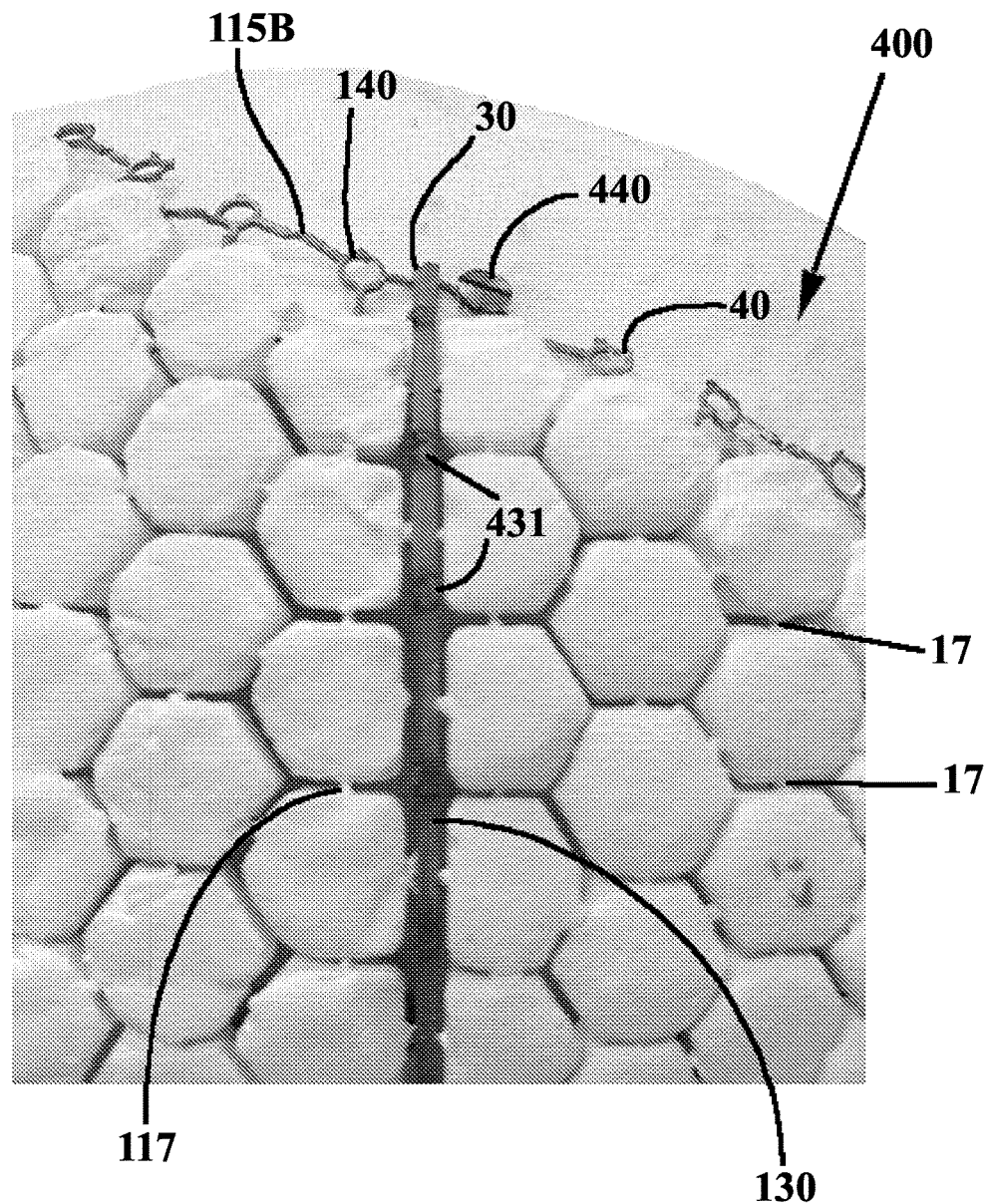
FIG. 10 shows an enlarged view of a portion of the view shown in FIG. 4.

After setting and hardening of the mosaic plate material, the implant section (210) is removed from mold (510). Thereafter, the implant section (210) is cut to the desired length and width, as necessary. For example, as best seen in FIGS. 4 and 10, the portion of the rim (30, 130, 230) extending across the top and bottom ends of the implant section is cut off along with portions of the rim extending along the sides of the implant section as necessary. In addition, wires (14, 114, 214), particularly longitudinally extending wires (14A, 114A, 214A), may be cut as necessary, to trim the implant section to the desired length. Similarly, selected ones of laterally extending wires (14B, 114B, 214B) may be cut as necessary, particularly to trim in implant section to the desired width, as seen on the far right side of FIG. 4. Since eyelets (40, 140, 240) are used to secure the implant to bone surrounding a defect, the mosaic plate material along the periphery of the implant is also removed such as by breaking the plates off of the support frame using pliers or other suitable implement in order to expose one or more of the eyelets about the periphery of the implant (400), as also seen in FIG. 4.

As also seen in FIGS. 4 and 10, during molding some cement will set and harden within channels (514), directly above the portions of wires (14, 114, 214) and struts (32, 132, 232) not located within plates (12, 112, 212). Such excess cement (17, 117, 217) is not depicted in FIGS. 1-3. When the implant section is deformed to a curved shape (i.e., after molding, and in some cases within an operating room), these portions of excess cement (17, 117, 217) will fracture rather than the plates (provided the implant section is not deformed too much).

Figure 13:
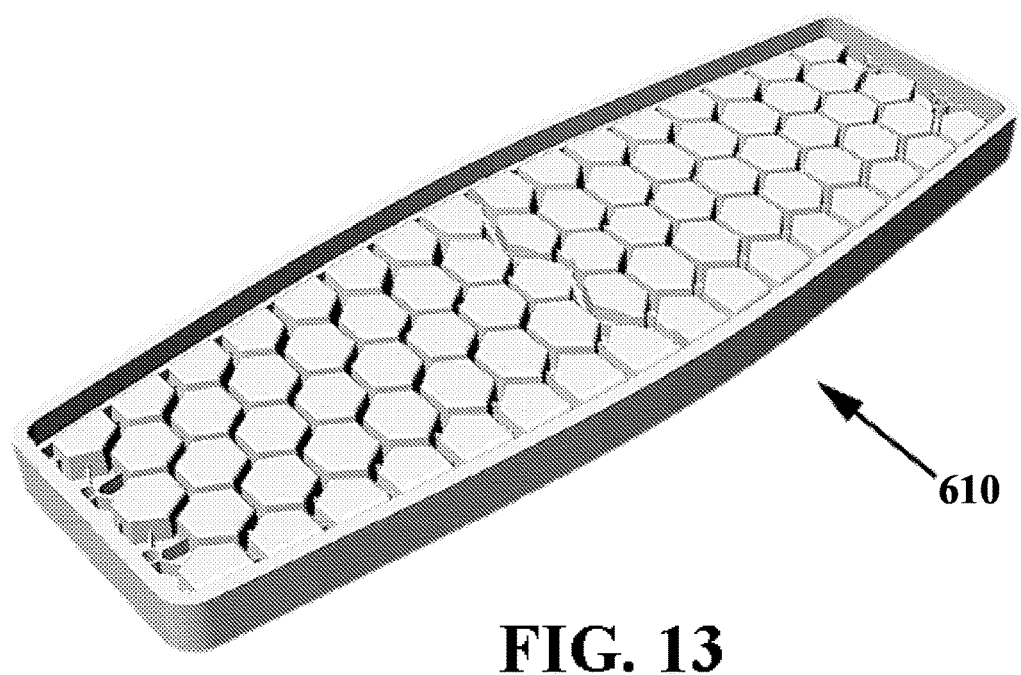
FIG. 13 depicts a perspective view of a negative mold suitable for forming the mold of FIG. 11.

As mentioned previously, mold (510) comprises silicone or other moldable material. FIG. 13 depicts a negative mold (610) which may be used to form mold (510) by a molding process.

Figure 14:
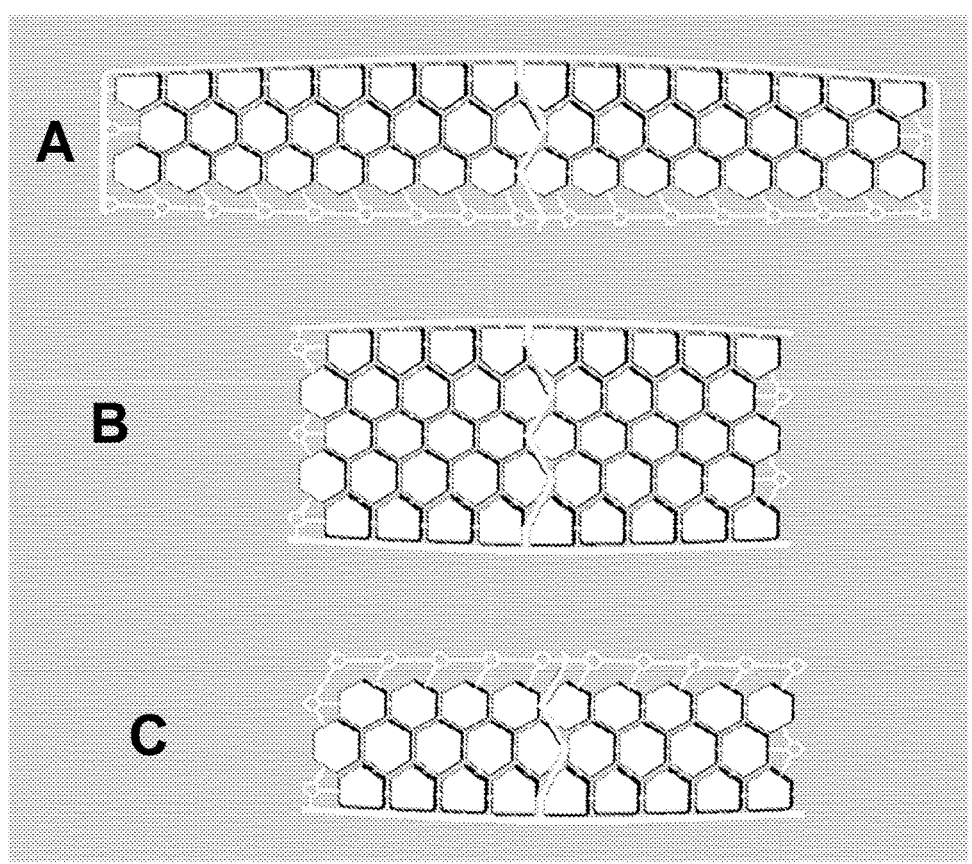
FIG. 14 depicts top plan views of three additional embodiments of implant sections having various configurations.

FIG. 14 depicts top plan views of three additional embodiments of implant sections having various configurations. The implant section of FIG. 14A is similar to implant section (110), however only three columns of mosaic plates are provided and one side of the wire mesh support frame has been omitted such that no rim is provided along that side of the implant. Instead, the rimless side of the implant includes a plurality of the retention eyelets. Effectively, wire mesh support frame (120) has been cut between the fourth and fifth columns of retention eyelets. This provides a narrower implant section suitable for use along an edge of a defect, as the eyelets may be used to secure the implant section in place. The implant section of FIG. 14B is similar to implant section (210), but considerably shorter with no rim along the ends of the implant section—only retention eyelets. Finally, the implant section of FIG. 14C is similar to that of FIG. 14A, only considerably shorter and with no rim extending along the ends or one side of the implant section. These various alternative shapes and configurations reduce waste as less material (particular the cement material) will be discarded, and are particularly suitable for use along an edge of a defect. By way of example only, these implant sections shown in FIG. 14 together with those previously described may have width of about 20 to about 60 mm, and lengths of about 60 to about 200 mm, as well as varying amounts of curvature or even irregular shapes. For example, instead of the opposing sides of the implant section having mirror image, gentle curvatures, the opposing sides may be the same direction of curvature, along with a greater degree of curvature (e.g., a curved implant section having a constant width rather than the width tapering towards the ends as shown, for example, in FIG. 3). The curvature may even vary along the length of the implant section.

Figure 15:
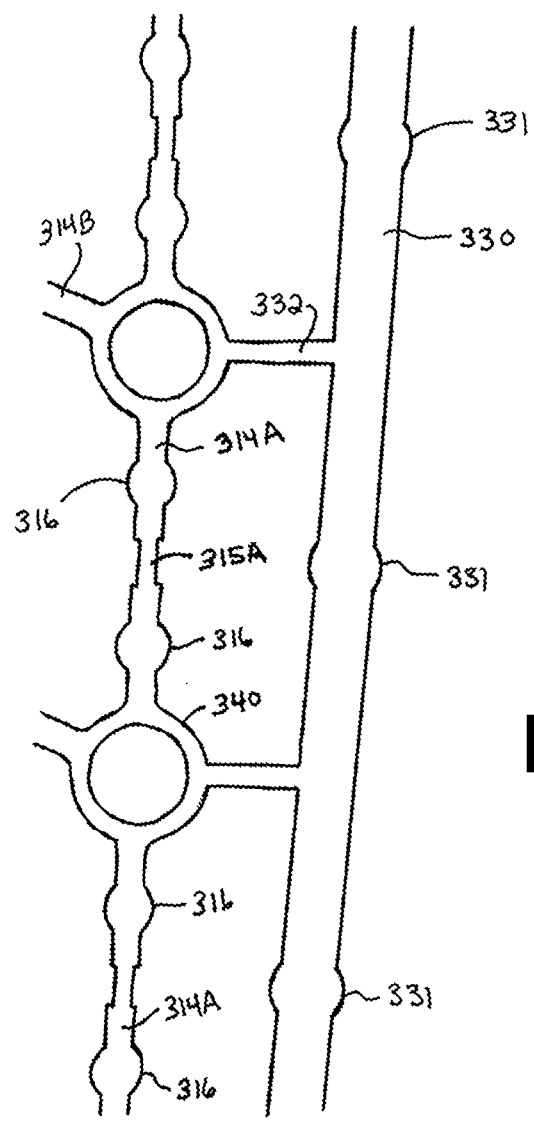
FIG. 15 depicts a portion of a further modified wire mesh support frame for use in any of the implant section embodiments described herein.

FIG. 15 depicts a portion of a further modified wire mesh support frame for use in any of the implant section embodiments described previously herein or described hereafter. In this embodiment, wire rim (330) includes a plurality of enlarged or widened regions (331) spaced along at least portions of the length of rim (330), particularly along the longitudinally extending sides of rim (330). Enlarged regions (331) can have any of a variety of shapes, sizes and locations, and that shown is merely exemplary of one embodiment. Regions (331) serve as fastening points for facilitating the attachment of two implant sections to one another along adjacent wire rims. Enlarged regions (331) this provide additional surface area at these fastening points, whereat the implant sections are attached to one another such as by using mechanical fasteners, biocompatible adhesives, welding, binding, etc. In one particular example, regions (331) provide welding spots that facilitate spot welding of one implant section to another by providing an enlarged weld contact area between implant sections. Regions (331) may be incorporated into any of the previously described implant section embodiments along one or more of the rims of the wire mesh support frame, and at one or more locations on such rims.

In addition to enlarged regions (331) on rim (330), similar enlarged regions (316) are provided along one or more of vertical wires (314A) which extend between adjacent retention eyelets (340). In the example shown in FIG. 15, a pair of enlarged regions (316) are provided on each vertical wire (314A), with each of the enlarged regions (316) located between the deformation zones provided by reduced-width regions (315A) and one of eyelets (340), as shown.

It will be understood that any number of enlarged regions (316) may be provided on vertical wires (314A), and one or more enlarged regions (316) may be provided on all or only a portion of vertical wires (314A). It is also contemplated that enlarged regions (316) may be provided instead of enlarged regions (331) on rim (330). Enlarged regions (316) serve the same purpose as enlarged regions (331), namely serving as fastening points (e.g., welding spots) which facilitate attachment of one implant section to another such as by providing an enlarged weld contact area between the implant sections. Enlarged regions (316) on vertical wires (314A) are particularly useful for spot welding implant sections such as those shown in FIGS. 14A and 14C to one another. Thus, even when the rim along one or both longitudinally extending edges of the implant section along with one or more columns of mosaic plates is omitted or removed, enlarged regions enlarged regions (316) still provide welding spots for facilitating spot welding of one implant section to another by providing an enlarged weld contact area between implant sections (e.g., for welding two implant sections of FIGS. 14 A and/or 14C to one another). Enlarged regions (316) can have any of a variety of shapes, sizes and locations, and that shown is merely exemplary of one embodiment. Regions (316) may be incorporated into any of the previously described implant section embodiments, as well those described below.

Figure 25:
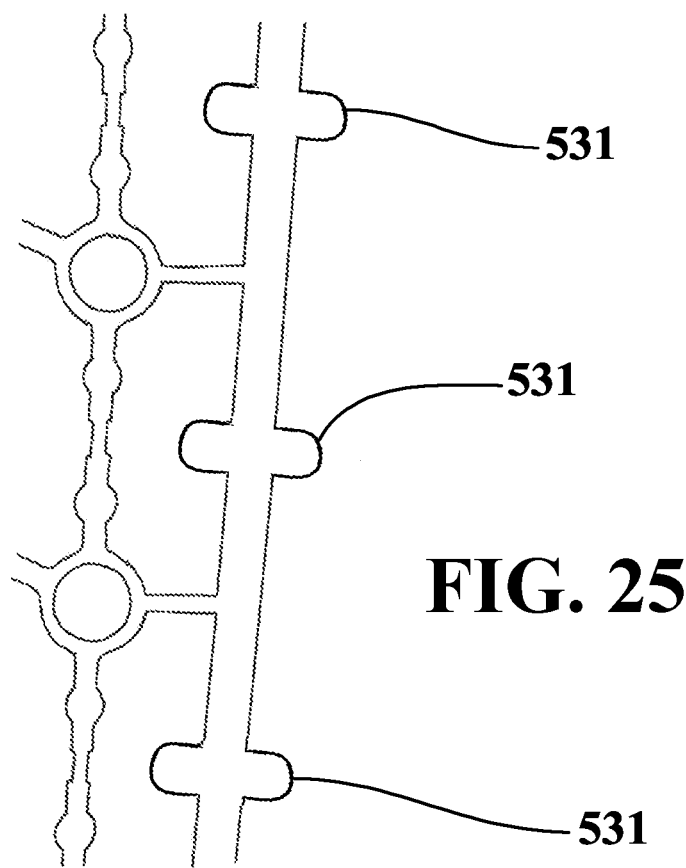
FIG. 25 is similar to FIG. 15, and depicts a portion of another alternative embodiment of a wire mesh support frame for use in any of the implant section embodiments described herein.

As an alternative to the bulbous shape of enlarged regions (331) shown in FIG. 15, FIG. 25 depicts enlarged regions (531) which have an elongated oval shape. When two implant sections are attached to one another (e.g., by welding) using enlarged regions (531) as fastening points (e.g., welding spots), the oval shape allows for additional slight curvature changes in the assembled implant. The increased length of the enlarged regions (531), both outwardly and inwardly from the rim, allow adjacent implant sections to be attached to one another such that their adjoining rims do not precisely overlap one another, for example.

As mentioned previously, in adjusting an implant to a specific defect the thickness $T_T$ of the mosaic plates (see FIG. 5) can be reduced by polishing or other material removal process, particularly along the periphery of the implant in order to improve implant fit and/or improve aesthetics. This may also be accomplished by forming the mosaic plates of an implant section to have varying thickness across the mosaic plates and/or across the implant section itself, such as by configuring a mold for the mosaic plates of the implant section accordingly.

Figure 16A:
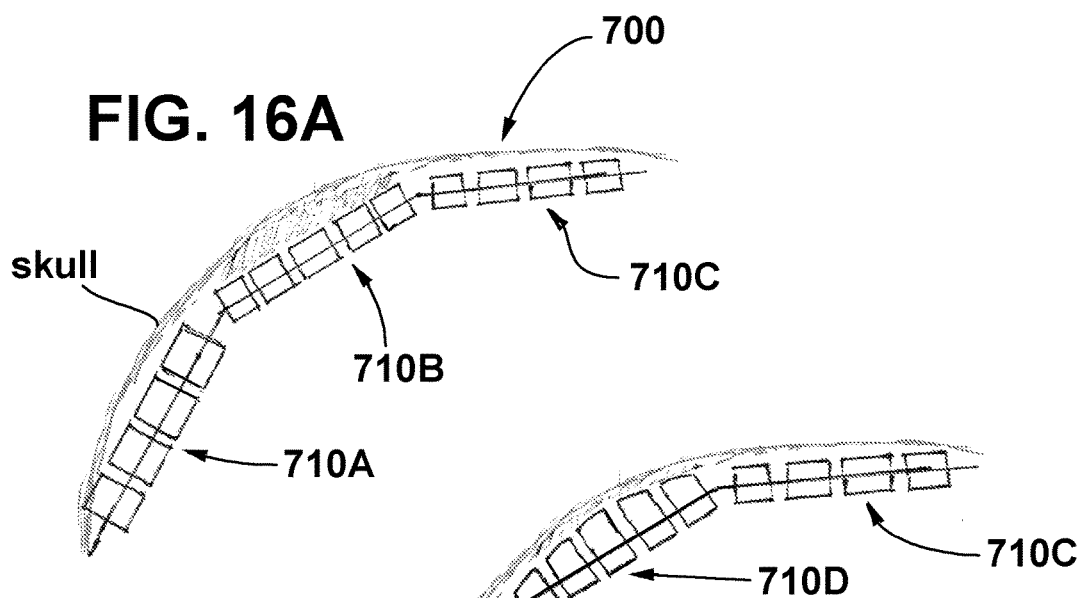
FIG. 16A is a schematic cross-sectional view depicting an implant implanted in a patient's skull.

By way of one specific example, FIG. 16A depicts a schematic cross-sectional view of an exemplary mosaic implant (700) secured to a patient's skull over the area of a very large defect. In this illustration, mosaic implant (700) comprises three implant sections (710A, 710B, 710C) which have been coupled together along their adjacent sides. Implant sections (710A, 710B, 710C) may be configured similarly to any of the implant sections previously described herein. As seen in FIG. 16A, when the surrounding skull or other bone adjacent the implant region has significant curvature, mosaic plates of uniform thickness will often result in implant (700) significantly deviating from the curvature of the skull (i.e., resulting in a flattened appearance in the area of the implant compared to the surrounding bone.

Figure 16B:
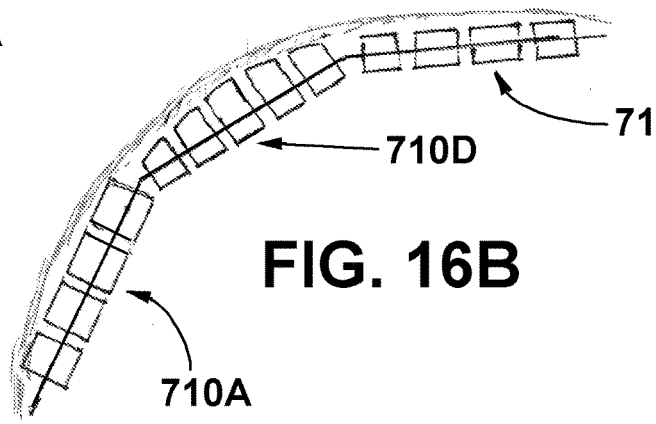
FIG. 16B is a schematic cross-sectional view similar to FIG. 16A, wherein an alternative embodiment of an implant section (710D) has replaced middle implant section (710B) of FIG. 16A.

In order to reduce or eliminate such a flattened region, the thickness of the mosaic plates may vary across the width and/or length of the implant section. In the embodiment shown in FIG. 16B, center implant section (710B) of FIG. 16A has been replaced by an implant section (710D) having mosaic plates which taper in thickness across the width of the implant. Thus, the mosaic plates at the center of the implant section are crowned, as shown, and the mosaic plates on either side thereof taper in thickness as shown. Thus, the mosaic plates of implant section (710D) are thickest at the middle of the implant section and narrowest at the outer sides of the implant section. Of course, it will be understood that the mosaic plates may taper in the lengthwise direction and or in one more other directions so as to better match the shape of the bone surrounding a patient's defect.

Figure 17:
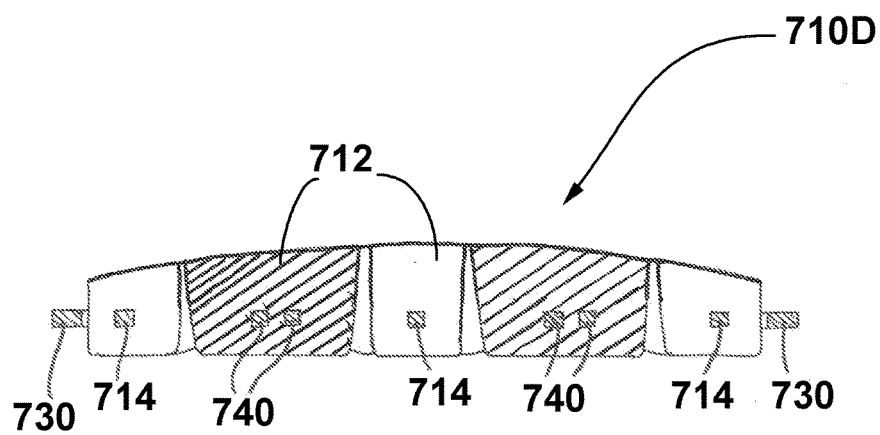
FIG. 17 is a cross-sectional view of the implant section (710D) of FIG. 16B, wherein the cross-sectional view is taken similarly to the cross-sectional view of FIG. 5 (i.e., across the width of the implant section).

FIG. 17 depicts a cross-sectional view of implant (710D), taken along the same line as that shown in FIG. 5. The additional reference numerals in FIG. 17 refer to the same components of like numerals in the preceding implant section embodiments (e.g., eyelet (740) and wires (714). Thus, apart from the tapered thickness of the mosaic plates (712), the construction of implant section (710D) is the same as implant sections (10, 110, 210).

Figure 18:
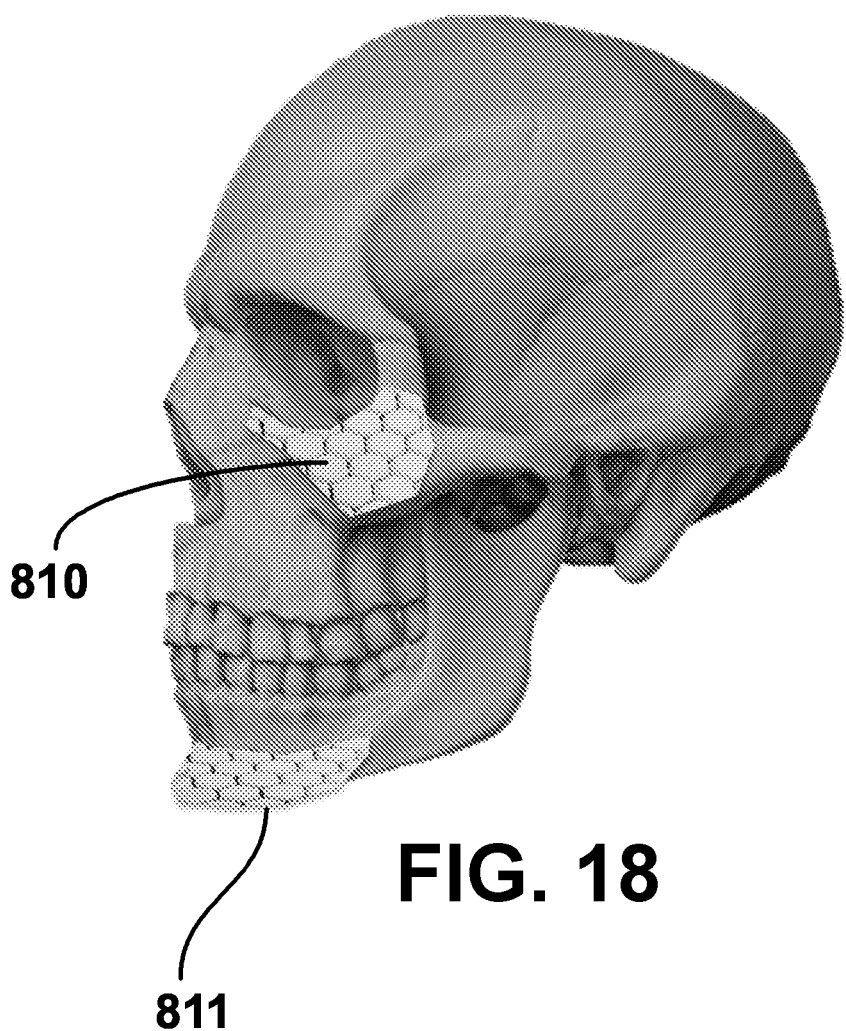
FIG. 18 depicts a mosaic implant (810) positioned over a defect in a patient's zygomatic (cheek) bone, and a second mosaic implant (811) positioned over a defect in a patient's mandible (chin).

The implants described herein, whether formed of a single or multiple implant sections may be used in treating a wide variety of bone defects or even for cosmetic purposes. By way of example, FIG. 18 depicts an implant (810) configured for use in repairing, restoring or augmenting a patient's zygomatic bone (cheek bone). Implant (810) is configured similar to implant section (10) described previously, but cut and shaped to the appropriate size (e.g., by cutting off unneeded portions of support frame (20) and removing or not molding unneeded mosaic plates (12)). Similarly, implant (811) in FIG. 18 is configured for use in repairing, restoring or augmenting a patient's mandible (chin). Once again, implant (811) may be formed from an implant section (10) which is shaped and configured in the desired size and shape. Of course, implants constructed in the manner described herein may be shaped and configured for any of a variety of other bones of a patient.

Figure 19:
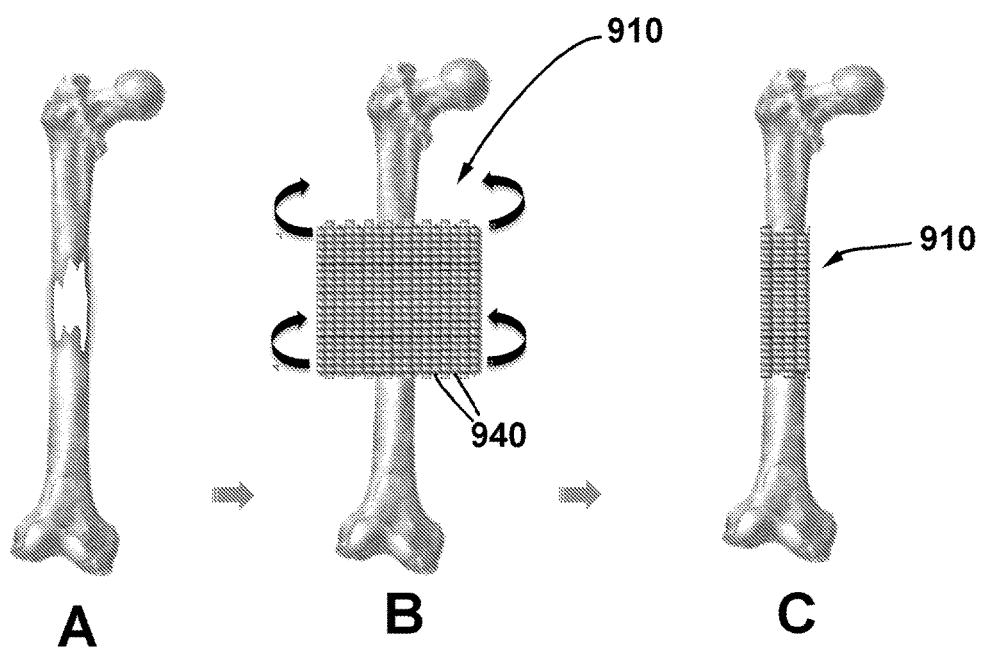
FIG. 19 depicts the process of using a mosaic implant (910) in the repair of a segmental long bone defect in a patient's femur.

The implants described herein may also be used to treat segmental bone defects, such as those occurring in long bones (e.g., a patient's femur). The implant (e.g., a single implant section) is wrapped around the bone defect and secured in place in the manner previously described (e.g., using screws). Any of the previously-described implants and implant sections may be used for this purpose. As an alternative, the hexagonal mosaic plates (12, 112, 212) may be replaced by staggered columns of rectangular mosaic plates. FIG. 19 depicts the process of wrapping an implant (910) around a segmental long bone defect in a femur.

Figure 20:
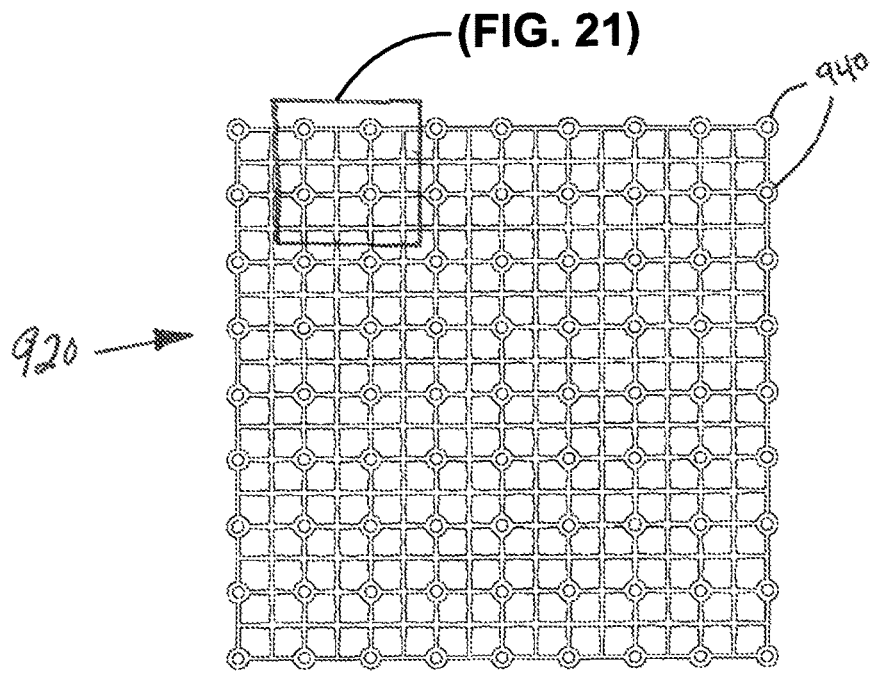
FIG. 20 is a top plan view of the wire mesh support frame used in the implant depicted in FIG. 19.
Figure 21:
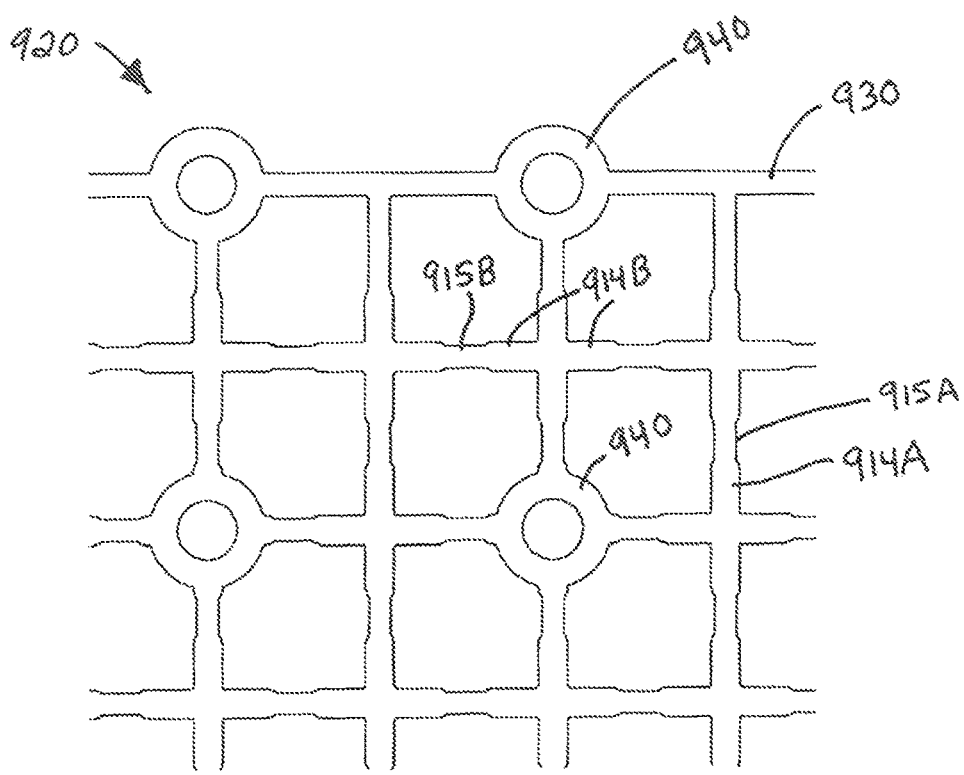
FIG. 21 is an enlarged top plan view of a portion of the wire mesh support frame of FIG. 20.
Figure 22:
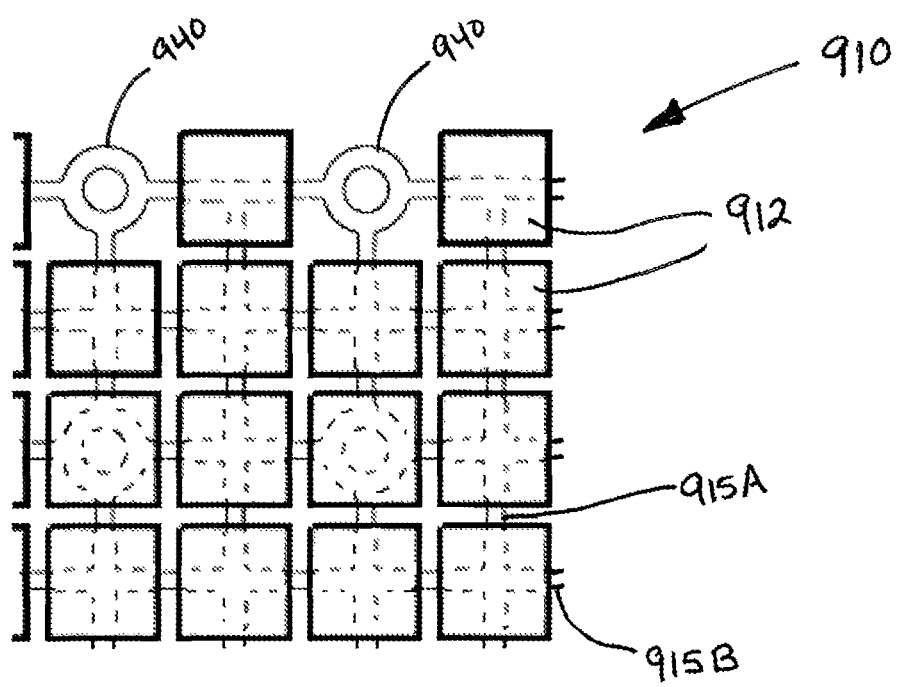
FIG. 22 is a view similar to FIG. 21, wherein the mosaic plates of the implant are shown in combination with the wire mesh support frame.

While implant (910) may be configured similar to, for example, implant section (10) described previously, FIGS. 20 and 21 depict an alternative arrangement particularly suited for use in segmental long bone defects. Here, the wire mesh support frame (920) is configured as a rectangular grid with wires (914) extending in either a horizontal or vertical direction, as shown. In this embodiment, however, retention eyelets (940) are not located at every intersection of wires (914). Instead, there are wire crossing regions located between adjacent eyelets (940). As shown in FIG. 22, mosaic plates (912) are located not only at eyelets (940) but also at the locations where wires (914) meet in a cross as well as the locations where a wire (914) intersects rim wires (930) which extend between the eyelets (940) located about the periphery of the implant (910). As also seen in FIG. 22, the eyelets (940) along one or more sides of the implant (910) may be left exposed (i.e., not enclosed or covered by a mosaic plate) such that these eyelets may be used to secure implant (910) to the patient's bone as shown in FIG. 19C (e.g., using one or more screws). In one embodiment, the eyelets (940) along the top and bottom edges of implant (910) are exposed, with mosaic plates (912) located between adjacent pairs of such eyelets.

Wires (914) of implant (910) also includes reduced-width deformation zones (915), as shown and as described previously. It is also contemplated that the wires (914) may have different widths and/or thicknesses to provide additional rigidity and support. For example, vertically extending wires (914A) may be wider and/or thicker than horizontally extending wires (914B) such that additional rigidity is provided in the direction parallel to the length of the long bone being repaired. Similarly, one or more support girders, as described previously may extend between adjacent columns or rows of mosaic plates in order to similarly provide rigidity and/or support, particularly in a direction parallel to the length of the long bone being repaired. It will be understood that any of the previously described materials and compositions, as well as manufacturing methods may be used for implant (910) as well as the implant described below.

Figure 23:
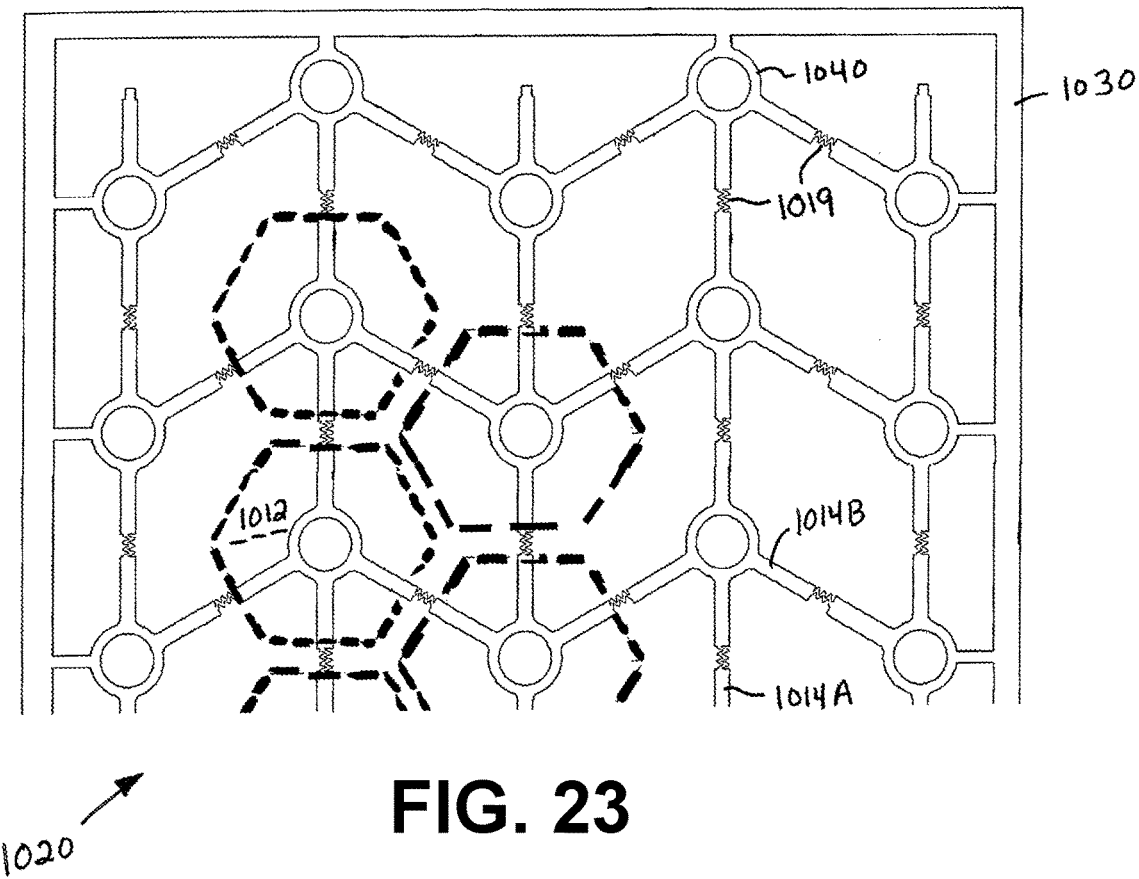
FIG. 23 is similar to the view shown in FIG. 9, and depicts an alternative wire mesh support frame wherein a plurality of the wires include an expandable (or stretchable) segment or region such that the support frame is expandable in one or more directions.
Figure 24:
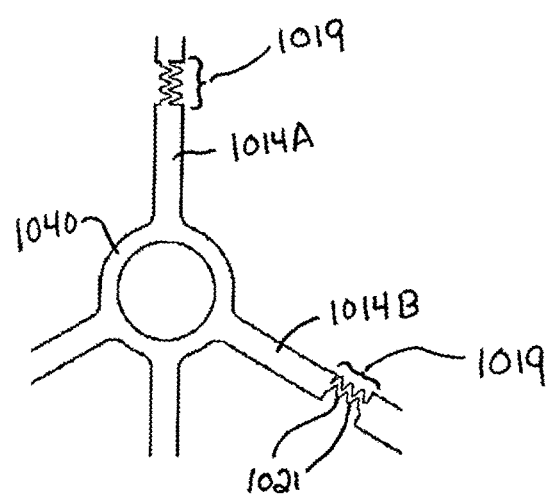
FIG. 24 depicts an enlarged portion of the wire mesh support frame of FIG. 23.

FIGS. 23 and 24 depict a further modified embodiment wherein deformation zones comprising a stretchable segment or region (1019) are provided on one or more of the wires (1014) of wire mesh support frame (1020). These stretchable segments (1019) comprise a plurality of pleats or crimps (1021), with three such pleats provided in the example shown. An implant formed using wire mesh support frame (1020) with mosaic plates (1012) formed thereon such that stretchable segments (1019) extend therebetween is particularly advantageous for use in children whose bones are still growing. Once implanted, as the patient's bone grows, the stretchable segments will expand along with the growing bone (particularly when portions or all of the outer rim of the wire mesh support frame are removed). The number and size of the pleats or crimps (1021) may be varied depending on the age of the patient, with more pleats or crimps (1021) used in implant for young children whose bones will be expected to grow more substantially, as additional pleats or crimps will allow for even greater expandability. It will also be understood that the stretchable segments may be provided on some or all of the wires (1014), depending on the anticipated direction of bone growth. In the example shown, the wire mesh support frame can expand lengthwise, widthwise and at angles parallel to the direction of wires (1014B).

Figure 26:
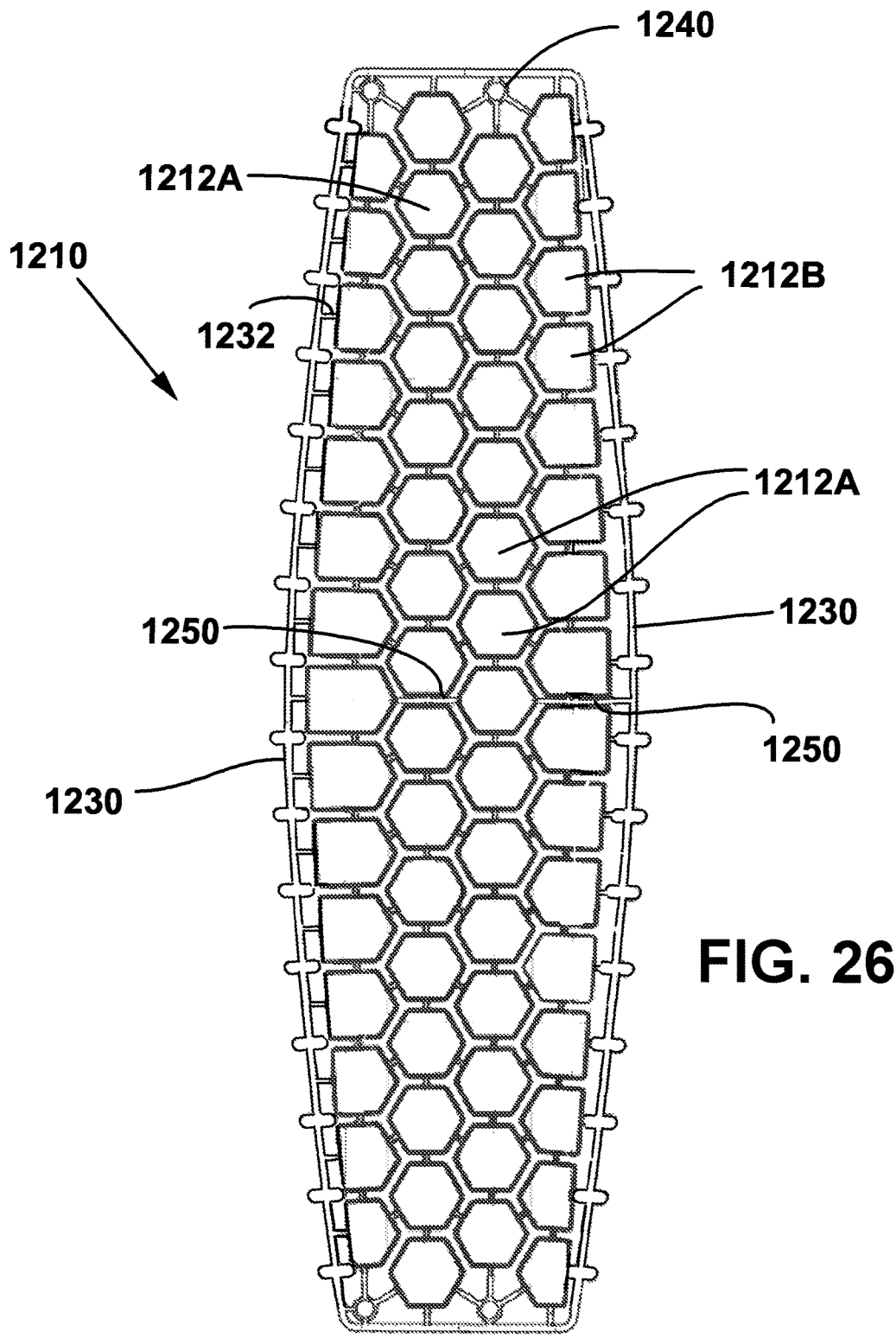
FIGS. 26 and 27 depict top plan views of still further embodiments of implant sections.
Figure 27:
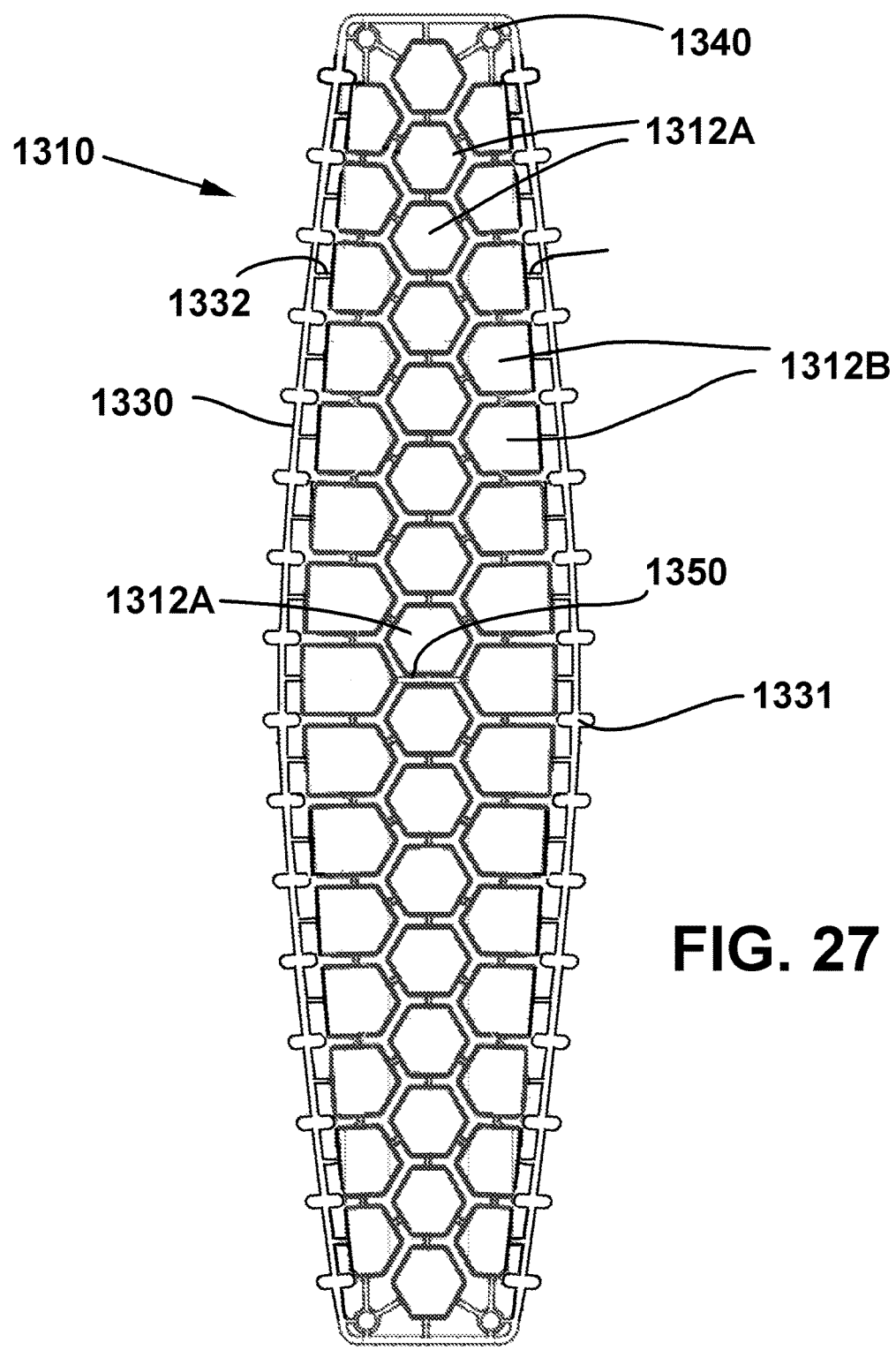
Figure 28:
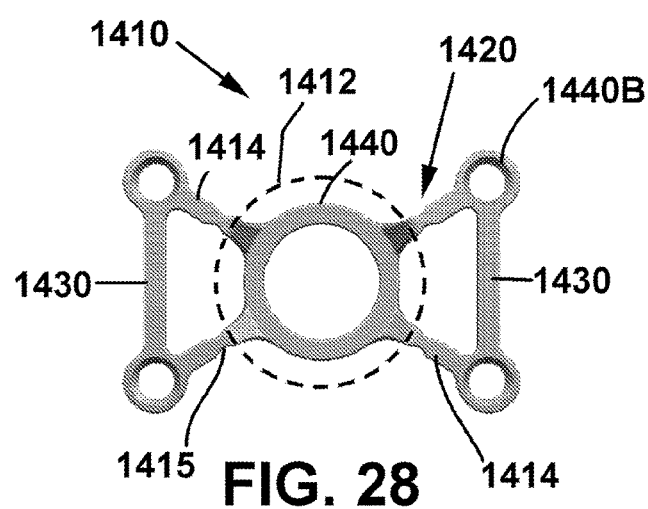
FIG. 28 depicts a top view of a wire mesh support frame of a bore hole implant, wherein the biocompatible plate (e.g., a hydraulic cement) is shown in dashed line.
Figure 29:
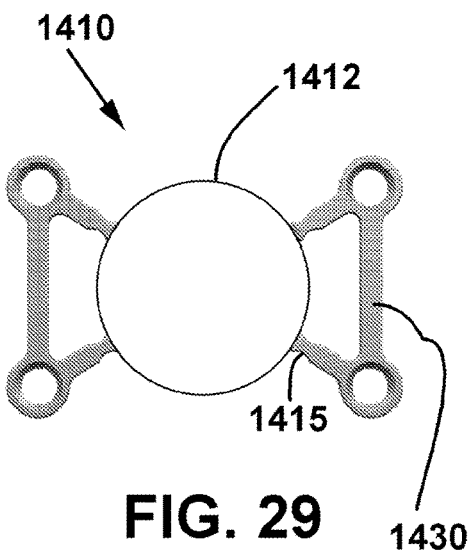
FIG. 29 depicts a top plan view of the bore hole implant of FIG. 28, including the round plate.
Figure 30:
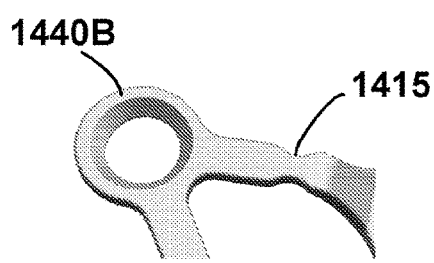
FIG. 30 depicts an enlarged view of a portion of the wire mesh support frame of FIG. 28.

FIGS. 26 and 27 depict still further alternative embodiments of implant sections (1210, 1310). These implant sections are constructed similarly to those previously described herein, such as implant sections (10, 110, 210) and include various features of similar reference numerals in FIGS. 1-10. Implant sections (1210, 1310) may also be fabricated in the manners described previously herein.

Unlike the previously described implant sections (10, 110, 210), implant section (1210) includes only four columns of mosaic plates—two interior columns of hexagonal plates (1212A) and two outer columns of pentagonal plates (1212B). As before, the columns of plates are staggered such that consistent gaps are provided between the edges of adjacent plates, as shown. Implant section (1310) includes only three columns of mosaic plates—one interior columns of hexagonal plates (1312A) and two outer columns of pentagonal plates (1312B). Implant sections (1210, 1310) provide additional configurations for assembled implants, as these implant sections (1210, 1310) may be combined with any of the implant sections (110, 210, 310) previously described herein.

In the particular examples shown, implant section (1210) has a width of about 41 mm at its center (i.e., at support girder (1250)) and implant section (1310) has a width of about 31 mm at its center (i.e., at support girder (1350)). As in implant sections (210, 310), the outermost edges of pentagonal outer plates (1212B, 1312B) are aligned with, and spaced inwardly from, wire rim (1130, 1230) by a generally constant distance, as shown in FIGS. 26 and 27. Of course, these sizes and the depicted curvatures of the sides of implants (1210, 1310) are merely exemplary, as any of a wide variety of sizes and curvatures/tapers may be provided in the implant sections.

FIGS. 28-37 depict further embodiments of implants (1410, 1510, 1610, 1710) suitable for filling a bore hole (also referred to as a burr hole) in a bone, particularly the skull. These implants are similar to those described in Applicant's U.S. Pub. No. 2013/0053900A1, published on Feb. 28, 2013, entitled "Implants And Methods For Using Such Implants To Fill Holes In Bone Tissue," as well as PCT Pub. No. WO 2013/027175, also published on Feb. 28, 2013, and entitled "Implants And Methods For Using Such Implants To Fill Holes In Bone Tissue." The foregoing U.S. and PCT publications are incorporated by reference herein.

As described in the publications referenced in the preceding paragraph, when it is necessary to remove a portion of a patient's skull, three (or more) bore holes are created. The bore holes are then joined by saw cuts that together with the bore holes form a continuous cut line through the skull, thereby releasing a bone flap from the rest of the skull. The bone flap can be lifted to allow access to the underlying tissue. When the bone flap is replaced, it is desirable not only to anchor it into place but also to at least partly fill the bore holes. Implants (1410, 1510, 1610, 1710) are adapted for such purpose.

Implants (1410, 1510, 1610, 1710) generally comprises a round plate (1412, 1512, 1612, 1712) (referred to as a plate in the references discussed above) and a wire mesh support frame (1420, 1520, 1620, 1720). Other implant plate shapes are also possible, for example, oval triangular, square, rectangular, pentagonal, hexagonal, etc. However, a circular shape will most closely match a circular bore hole. As with the mosaic implants described previously herein, the wire mesh support frame (1420, 1520, 1620, 1720) includes wire segments (e.g., wires (1414, 1514, 1614, 1714) which are joined to one another such as via eyelets (1440, 1540) in implants (1410, 1510) or at juncture (1641, 1741) in implants (1610, 1710).

Portions of the wire mesh support frames (1420, 1520, 1620, 1720) are enclosed the round plate (1412, 1512, 1612, 1712), as shown. In implants (1410, 1510), the eyelet (1440, 1540) is enclosed within the plate (1412, 15 12) along with portions of the four wires (1414, 1514) extending outwardly therefrom. The wire mesh support frame (1420, 1520, 1620, 1720) and round plate (1412, 1512, 1612, 1712) are made from any of the variety of materials, using the methods previously described with respect to the wire mesh support frames and biocompatible mosaic plates of the previously described implant sections (10, 110, 210).

Wires (1414, 1514, 1614, 1714) extend outwardly away from the interior of the plate, and terminate in fastening points adapted for securing the implant to bone surrounding a bore hole. In the embodiments shown, the fastening points comprise retention eyelets (1440B, 1540B, 1640, 1740). Implants (1410, 1510) further include a pair of wire rims (1430, 1530) which extend between and connect a pair of eyelets (1440B, 1540B) on opposite sides of the implant (1410, 1510). As before, the rims (1430, 1530) are depicted as being wider than the wires (1414, 1514) which extend into the plate (1412, 1512). Implants (1610, 1710) also include wire rims (1630, 1730), but in these embodiments the rims (1630, 1730) extend between and connect adjacent eyelets (1640, 1740) such that the rims and eyelets encircle the plate (1620, 1720). In the implant (1610) shown in FIG. 36, the wires (1614) extending outward of the plate (1620) intersect and are connected to the rims (1630) intermediate of adjacent eyelets (1640). In the implant (1710) shown in FIG. 37, the wires (1714) extending outward of the plate (1720) intersect and are connected to the eyelets (1640).

Figure 37:
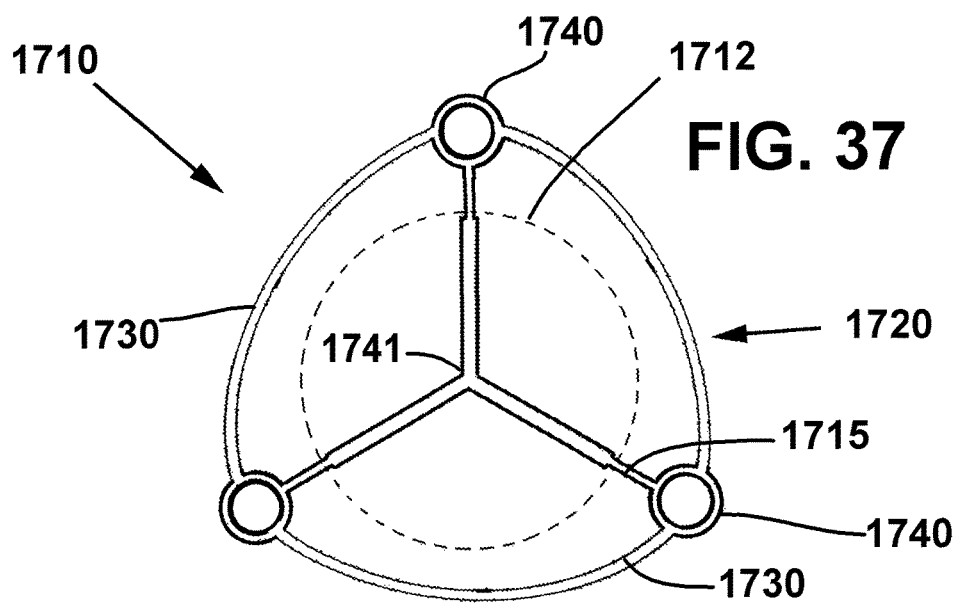
FIG. 37 depicts a top view of a still further embodiment of a wire mesh support frame of a bore hole implant, wherein the biocompatible plate is shown in dashed line.

Also, in order to reduce the outer circumference of the implant (1710) shown in FIG. 37 while still providing deformation zones for adjusting the implant (as described below), the rims (1730) are not arranged in a circular pattern like those of implant (1610). Instead, the rims (1730) are arranged similar to a Reuleaux triangle.

Figure 31:
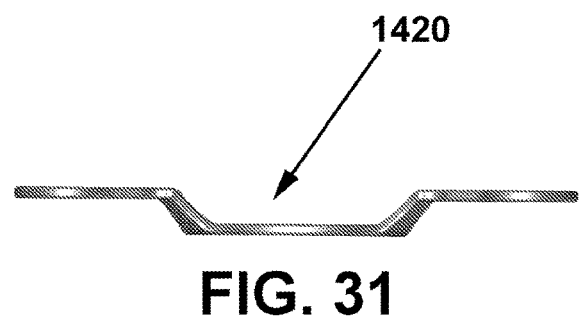
FIG. 31 depicts a side view of the wire mesh support frame of FIG. 28.
Figure 32:
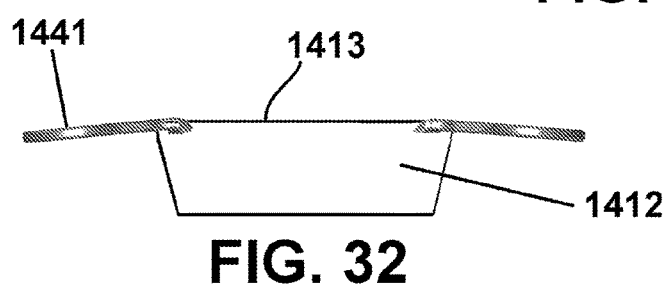
FIG. 32 depicts a side view of the bore hole implant of FIG. 29.
Figure 33:
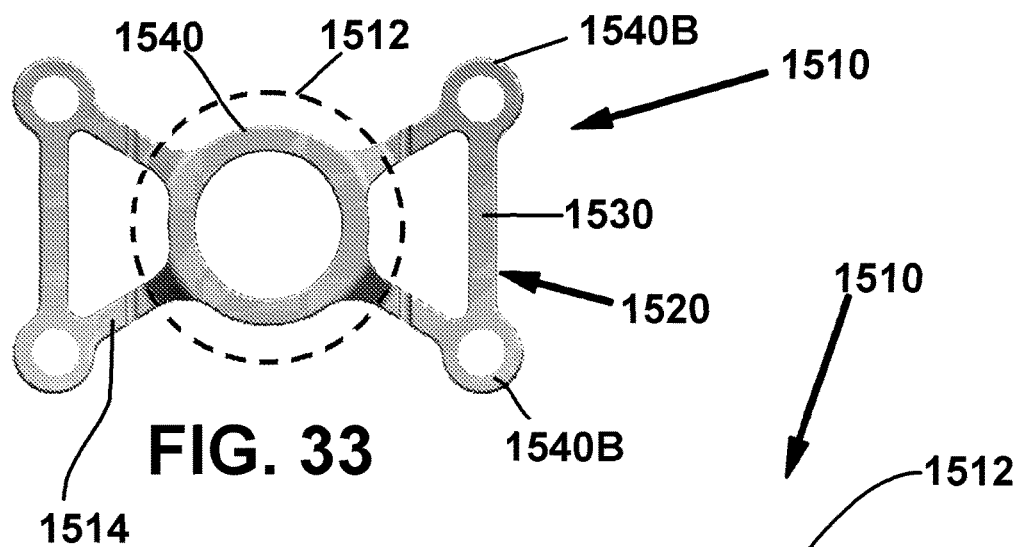
FIG. 33 depicts a top view of another embodiment of a wire mesh support frame of a bore hole implant, wherein the biocompatible plate (e.g., monetite) is shown in dashed line.
Figure 34:
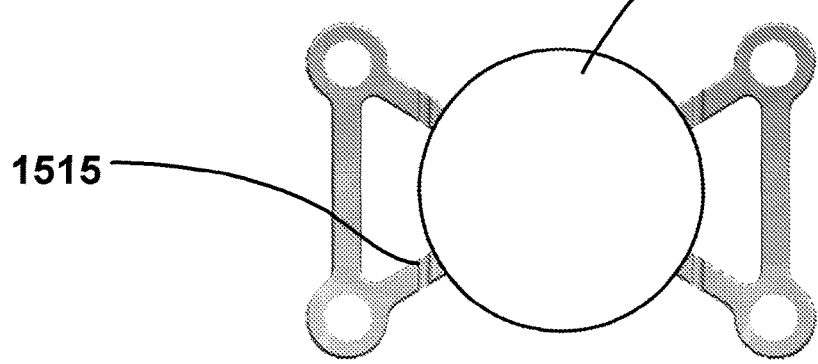
FIG. 34 depicts a top plan view of the bore hole implant of FIG. 33, including the round plate.
Figure 35:
FIG. 35 depicts an enlarged view of a portion of the wire mesh support frame of FIG. 33.
Figure 36:
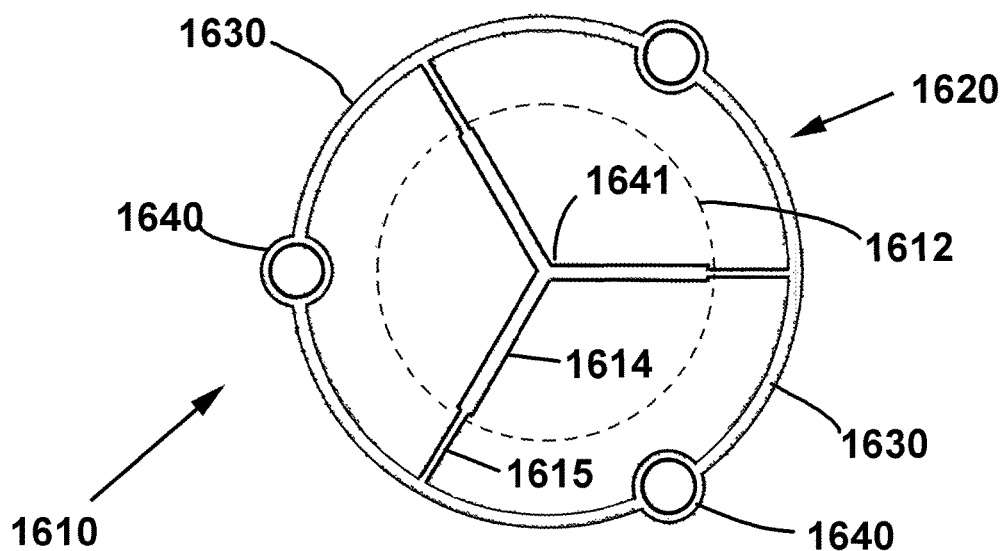
FIG. 36 depicts a top view of yet another embodiment of a wire mesh support frame of a bore hole implant, wherein the biocompatible plate is shown in dashed line.

As best seen in the side view of implant (1410) in FIGS. 31 and 32, the central region of the wire mesh support frame enclosed in the plate (1412) is depressed such that when eyelet (1440) is positioned in the middle of plate (1412), the upper surface (1413) of the plate (1412) will generally be level with the upper surface (1441) of the retention eyelets (1440B). The implants (1510, 1610, 1710) shown in FIGS. 33-37 are configured in a similar manner. This allows the implant to be inserted into a bore hole, and screws or other fasteners driven into the surrounding bone through the retention eyelets, such that the upper surface of the plate will be flush (or nearly flush) with the outer surface of the surrounding bone. However, as seen in FIG. 32, the wires (1414) are also configured to be deformable, such as being bent downward as shown. This allows the implant to be deformed in order to match the curvature of the patient's skull.

In order to facilitate deformation of the wires (1414, 1514, 1614, 1714), deformation zones are once again provided on these wires. In the embodiment shown in FIGS. 28-32, reduced width regions (1415) are provided on wires (1414) exterior to plate (1412) in order to facilitate bending of the wires (1414) as needed. In the embodiment shown in FIGS. 33-35, the deformation zones comprise reduced thickness regions (1515) provided on wires (1514) by forming a small cutout in the bottom surface of the wires (1514) exterior to plate (1512) in order to facilitate bending of the wires (1414) as needed. And in the embodiments of FIGS. 36 and 37, reduced width sections (1615, 1715) are provided for the portion of wires (1614, 1714) exterior to plate (1612, 1712).

Finally, as seen in FIG. 32, the plate (1412) is in the form of a tapered cylinder, with the smallest diameter at the bottom of the plate. This facilitates insertion of the plate into a bore hole in a patient.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required.

What is claimed is:

1. A mosaic implant, comprising:
   (a) a plurality of spaced-apart biocompatible mosaic plates, with a gap between adjacent plates; and
   (b) a wire mesh interconnecting the plates with one another, said wire mesh comprising a plurality of wire segments and a plurality of eyelets enclosed within said plates, wherein the wire segments are connected to each other by said eyelets and extend between adjacent plates;
   wherein at least a portion of said wire segments include deformation zones located in the gap between adjacent mosaic plates which facilitate deformation of the mosaic implant so as to reduce the risk of ceramic fracture upon bending of said wire mesh.

2. The mosaic implant of claim 1, wherein said deformation zones are chosen from the group consisting of: reduced-thickness regions, reduced-width regions and pleated regions.

3. The mosaic implant of claim 2, wherein at least a portion of said deformation zones comprise pleated regions.

4. The mosaic implant of claim 3, wherein said pleated regions have a reduced width.

5. The mosaic implant of claim 2, wherein at least a portion of said deformation zones comprise reduced-thickness regions.

6. The mosaic implant of claim 2, wherein at least a portion of said deformation zones comprise reduced-width regions.

7. The mosaic implant of claim 2, wherein said deformation zones are located on each of the wire segments that interconnect adjacent plates.

8. The mosaic implant of claim 1, wherein said implant further comprises a plurality of fastening points which facilitate attachment of the mosaic implant in a patient.

9. The mosaic implant of claim 2, wherein said implant further comprises a plurality of exposed eyelets located about the periphery of the implant, said eyelets adapted to receive a fastener for securing the implant to bone.

10. The mosaic implant of claim 1, wherein at least a portion of the mosaic implant is conformed to a substantially spheroidal surface.

11. The mosaic implant of claim 1, wherein said biocompatible mosaic plates comprise a hydraulic cement composition.

12. The mosaic implant of claim 11, wherein said biocompatible mosaic plates comprise a cement comprising at least 55 wt. % monetite.

13. The mosaic implant of claim 1, wherein said implant includes a support frame comprising said wire mesh and a wire rim which extends about at least a portion of the periphery of the implant.

14. A mosaic implant for correcting a bone defect in a patient, comprising:
   (a) a plurality of biocompatible mosaic plates;
   (b) a support frame including a wire mesh interconnecting the plates with one another, the wire mesh comprising a plurality of wire segments interconnected by a plurality of eyelets enclosed within said plates;
   wherein said support frame further comprises a wire rim extending about at least a portion of the periphery of the support frame and connected to a portion of said eyelets by wire struts.

15. The mosaic implant of claim 14, wherein the wire rim extends around the entire periphery of the support frame.

16. The mosaic implant of claim 15, wherein at least a portion of the wire rim is curved.

17. The mosaic implant of claim 16, wherein said plurality of plates include a central portion of plates having a hexagonal shape, and an outer portion of plates having an irregular pentagonal shape.

18. The mosaic implant of claim 17, wherein the outermost edges of the outer portion of plates are curvilinearly aligned with one another.

19. The mosaic implant of claim 14, wherein said eyelets are round.

20. The mosaic implant of claim 14, wherein said eyelets are hexagonal.

21. The mosaic implant of claim 15, wherein said eyelets are hexagonal.

22. The mosaic implant of claim 14, wherein said wire mesh includes deformation zones located between adjacent mosaic plates which facilitate deformation of the mosaic implant, said deformation zones chosen from the group consisting of: reduced-thickness regions, reduced-width regions and pleated regions.

\* \* \* \* \*